(12) United States Patent
Meade et al.

(10) Patent No.: US 8,173,860 B2
(45) Date of Patent: May 8, 2012

(54) NON-HUMAN TRANSGENIC MAMMAL EXPRESSING A HUMAN FCRN ON ITS MAMMARY GLAND CELLS AND EXPRESSING A TRANSGENIC PROTEIN-HUMAN FC-DOMAIN FUSION

(75) Inventors: Harry M. Meade, Newton, MA (US); Daniel Pollock, Medway, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 398 days.

(21) Appl. No.: 11/788,775

(22) Filed: Apr. 20, 2007

(65) Prior Publication Data

US 2008/0063780 A1 Mar. 13, 2008

Related U.S. Application Data

(60) Provisional application No. 60/745,287, filed on Apr. 21, 2006.

(51) Int. Cl.
*A01K 67/00* (2006.01)
*C12P 21/00* (2006.01)

(52) U.S. Cl. .................................. 800/14; 800/5; 800/6

(58) Field of Classification Search ........................ None
See application file for complete search history.

(56) References Cited

U.S. PATENT DOCUMENTS

| 5,416,017 | A | | 5/1995 | Burton | |
|---|---|---|---|---|---|
| 5,965,789 | A | * | 10/1999 | Lubon et al. | 800/14 |
| 6,924,412 | B1 | | 8/2005 | de Groot | |
| 2004/0117863 | A1 | * | 6/2004 | Edge et al. | 800/7 |
| 2006/0272036 | A1 | * | 11/2006 | Hammarstrom et al. | 800/7 |

FOREIGN PATENT DOCUMENTS

| WO | WO 94/23046 | 10/1994 |
|---|---|---|
| WO | WO 97/07669 | 3/1997 |
| WO | WO 01/57088 A1 | 8/2001 |

OTHER PUBLICATIONS

Alexander et al., Isolation and Characterization of the Bovine K-Casein Gene, Eur. J. Biochem. 1988; 178: 395-401.
Alzari, P.M. et al., Three-Dimensional Structure of Antibodies. Ann. Rev. Immunol. 1988 6: 555-580.
Baguisi A, et al., (1999) Production of Goats by Somatic Cell Nuclear Transfer, Nature Biotech. 17: 456-461.
Bird et al,. Single-chain antigen-binding proteins. (1988) Science. 242: 423-426.
Brignon et al., Preparation and Amino Acid Sequence of Human Acid Sequence of Human K-Casein, FEBS Letts. 1985; 188: 48-54.
Campbell et al., Comparison of the Whey Acidic Protein Genes of the Rat and Mouse, Nucleic Acids Res. 1984; 12: 8685-8697.
Campbell et al., Sheep cloned by nuclear transfer from a cultured cell line. Nature. Mar. 7, 1996; 380 (6569): 64-66.
Chung et al., A 5' element of the chicken beta-globin domain serves as an insulator in human erythroid cells and protects against position effect in Drosophila. 1993. Cell. 74, 505-514.
Cianga P, et al. Identification and function of neonatal Fc receptor in mammary gland of lactating mice. Eur J Immunol. 1999; 29:2515-23.
Cibelli et al., Cloned transgenic calves produced from nonquiescent fetal fibroblasts. Science. May 22, 1998; 280 (5367): 1256-1258.
Clark et al., Expression of Human Anti-hemophilic Factor IX in the Milk of Transgenic Sheep, (1989) Bio/Technology 7: 487-492.
Colcher D, et al., Effects of Genetic Engineering on the Pharmacokinetics of Antibodies. QJ Nucl Med 1999; 43:132-9.
Costa et al., Transcriptional control of the mouse prealbumin (transthyretin) gene: both promoter sequences and a distinct enhancer are cell specific. 1986, Mol. Cell. Biol. 6: 4697-4708.
Crowe J. S., et al., Humanized Monoclonal Antibody Campath-1H: Myeloma Cell Expression of Genomic Constructs, Nucleotide Sequence of cDNA Constructs and Comparison of Effector Mechanisms of Myeloma and Chinese Hamster Ovary Cell Derived Material. Clin Exp Immunol (1992); 87: 105-110.
Davis, G. T. et al., Single Chain Antibody (SCA) Encoding Genes: One-Step Construction and Expression in Eukaryotic Cells. Bio/Technol. 1991 9: 165-69.
DiTullio et al., Production of cystic fibrosis transmembrane conductance regulator in the milk of transgenic mice. Biotechnology (NY). Jan. 1992;10 (1) :74-77.
Ebert et al., Induction of human tissue plasminogen activator in the mammary gland of transgenic goats. Biotechnology (NY). Jul. 1994; 12 (7): 699-702.
Edmunds et al., Transgenically produced human antithrombin: structural and functional comparison to human plasma-derived antithrombin. Blood. Jun. 15, 1998; 91 (12): 4561-4571.
Figueiredo and Brownlee, Cis-acting elements and transcription factors involved in the promoter activity of the human factor VIII gene. 1995, J. Biol. Chem. 270: 11828-11838.
Ghetie V., et al., FcRn: the MHC Class I-related Receptor that is More than an IgG Transporter, Immunol Today. (1997); 18: 592-598.
Gordon et al., Production of Human Tissue Plasminogen Activator in Transgenic Mouse Milk. (1987) Bio/Technology 5: 1183-1187.
Gorodetsky et al., Isolation and Characterization of the Bos taurus beta-Casein Gene, Gene 1988; 66: 87-96.
Hall et al., Organization and sequence of the human alpha-lactalbumin gene. Biochem J. Mar. 15, 1987; 242(3): 735-42.
Holliger et al., Diabodies: small bivalent and bispecific antibody fragments. (1993) Proc. Natl. Acad. Sci. USA 90: 6444-6448.
Huston et al., Protein engineering of antibody binding sites: recovery of specific activity in an anti-digoxin single-chain Fv analogue produced in *Escherichia coli*. (1988) Proc. Natl. Acad. Sci. USA 85: 5879-5883.
Ivanov et al., Molecular Cloning of Bovine beta-Lactoglobulin cDNA, Biol Chem Hoppe Seyler 1988; 369 (6): 425-9.
Jakobovits, A. L. et al., Expression of Human Immunoglobulin Loci-Derived YACs in Mice: Towards Mice Producing a Large Repertoire of Human Antibodies. J. Cell. Biochem. Abstr. Suppl. 18D 1994 (Abstract T-017):185.

(Continued)

*Primary Examiner* — Deborah Crouch
(74) *Attorney, Agent, or Firm* — Wolf, Greenfield & Sacks, P.C.

(57) ABSTRACT

The invention provides, in part, methods for the production of proteins in a transgenic non-human mammal, wherein the proteins are transported from the blood to the mammary gland for secretion in milk. The transport of the protein to the mammary gland and/or milk is facilitated by binding to a transport receptor in the mammary gland.

12 Claims, 4 Drawing Sheets

OTHER PUBLICATIONS

James et al., Restricted distribution of tetraploid cells in mouse tetraploid<==>diploid chimaeras. Dev Biol. Jan. 1995; 167(1): 213-26.

Jamieson et al., Cloning and Nucleotide Sequence of the Bovine, beta-Lactoglobulin Gene, Gene 1987; 61: 85-90.

Jones, et al., The Rat Casein Multigene Family—Fine Structure and Evolution of the beta-Casein Gene, J. Biol. Chem. 1985; 260: 7042-7050.

Junghans R.P. and Anderson C.L., The Protection Receptor for IgG Catabolism is the B2-Microglobulin-Containing Neonatal Intestinal Transport Receptor, Proc Natl Acad Sci USA. (1996); 96:5512-5516.

Junghans R. P., Finally! The Brambell Receptor (FcRB): Mediator of Transmission of Immunity and Protection from Catabolism for IgG, Immunol Res. (1997); 16: 29-57.

Kacskovics, Fc receptors in livestock species. Vet. Immunology and Immunopathology, 102 (2004) 351-362.

Kato et al., Eight calves cloned from somatic cells of a single adult. Science, vol. 282 (1998) 2095-2098.

Kim K.J. et al., Net Absorption of IgG via FcRn-Mediated Transcytosis Across Rat Alveolar Epithelial Cell Monolayers. Am J Physiol Lung Cell Mol Physiol. (2004) 287(3):L616-L622.

Kuroiwa Y., et al., Manipulation of Human Minichromosomes to Carry Greater than Megabase-Sized Chromosome Inserts. Nat Biotechnol. (2000); 18: 1086-1090.

Lantto J. et al., Chain Shuffling to Modify Properties of Recombinant Immunoglobulins. Methods Mol. Biol. (2002) 178: 303-316.

Leach J. L. et al., Isolation from Human Placenta of the IgG Transporter, FcRn, and Localization to the Syncytiotrophoblast: Implications for Maternal-Fetal Antibody Transport, J. Immunology, (1996) 157(8): 3317-3322.

Mayer B. et al., Redistribution of the sheep neonatal Fc receptor in the mammary gland around the time of parturition in ewes and its localization in the small intestine of neonatal lambs. Immunology (2002) 107: 288-296.

Mercier and Vilotte, Structure and function of milk protein genes. J. Dairy Sci. 76, 3079-3098 (1993).

Ober et al., Differences in promiscuity for antibody-FcRn interactions across species: implications for therapeutic antibodies. Inter Immunol. 13: 1551-59 (2001).

Ober, R.J. et al., Exocytosis of IgG as Mediated by the Receptor, FcRn: an Analysis at the Single-Molecule Level, Proc. Natl. Acad. Sci. USA. (2004) 101: 11076-11081.

Padlan, E. A., Anatomy of the Antibody Molecule, Mol. Immunol. 31(3): 169-217 (1994).

Palombella V. J. et al., FCRN-mediated pulmonary delivery of interferon alpha FC-fusion protein in non-human primates. Hepatology, Williams and Wilkins, Baltimore, MD. vol. 38 (4) Suppl. 1, 2003, p. 277. Abstract.

Pinkert et al., An albumin enhancer located 10 kb upstream functions along with its promoter to direct efficient, liver-specific expression in transgenic mice. Genes Dev. 1987, 1: 268-276.

Poljak, R. J. et al., Production and structure of diabodies (1994) Structure 2: 1121-1123.

Praetor et al., Beta2-Microglobulin is important for cell surface expression and pH-dependent IgG binding of human FcRn. Journal of Cell Science. vol. 115, No. 11, 2002, 2389-2397.

Reff M. E., et al., Depletion of B cells In Vivo by a Chimeric Mouse Human Monoclonal Antibody to CD20. Blood (1994); 83: 435-445.

Richards, et al., Construction and Preliminary Characterization of the Rat Casein and alpha-Lactalbumin cDNA Clones, J. Biol. Chem. 1981; 256: 526-532.

Schnieke et al., Human factor IX transgenic sheep produced by transfer of nuclei from transfected fetal fibroblasts. Science, vol. 278. (1997), 2130-2133.

Schwartz J. et al., Structural basis for co-stimulation by the human CTLA-4/B7-2 complex. Nature 401:604-607, 2001.

Selgrath, et al., Collection and transfer of microinjectable embryos from dairy goats. Theriogenology, (1990) 34 (6): 1195-1205.

Soulier et al., Expression analysis of ruminant alpha-lactalbumin in transgenic mice: developmental regulation and general location of important cis-regulatory elements. FEBS Lett. Feb. 1992 297 (1-2): 13-18.

Stewart, et al., Nucleotide sequences of bovine alpha S1- and kappa-casein cDNAs. Nucleic Acids Res. 1984; 12: 3895-3907.

Vilotte, et al., Complete Nucleotide Sequence of Bovine alpha-Lactalbumin Gene: Comparison with Its Rat Counterpart, Biochimie 1987; 69: 609-620.

Wagner S. D., et al., Antibodies Generated from Human Immunoglobulin Miniloci in Transgenic Mice. Nucleic Acids Res., (1994); 22: 1389-1393.

Wakayama et al., Full-term development of mice from enucleated oocytes injected with cumulus cell nuclei. Nature, vol. 394 (1998), 369-374.

Waldmann, Monoclonal antibodies in diagnosis and therapy. 1991, Science 252:1657-1662.

Ward et al., Binding activities of a repertoire of single immunoglobulin variable domains secreted from *Escherichia coli*. (1989) Nature 341: 544-546.

Wells et al., Production of cloned lambs from an established embryonic cell line: a comparison between in vivo- and in vitro-matured cytoplasts. Biol. Reprod., vol. 57 (1997): 385-393.

Whitlow M.B. et al., An Improved Linker for Single-Chain Fv With Reduced Aggregation and Enhanced Proteolytic Stability. Protein Eng. (1993) 6(8): 989-995.

Worn A., et al., Stability Engineering of Antibody Single-Chain Fv fragments. J Mol Biol 2001; 305: 989-1010.

Yu-Lee, et al., The Rat Casein Multigene Family, J. Biol. Chem. 1983; 258: 10794-10804.

Alexander et al., Nuc Ac Res 1989, 17 (16): 6739.

Lu et al., Immunology 2007, 122: 401-8.

* cited by examiner

FLOWCHART OF AN EMBODIMENT OF THE CURRENT INVENTION

GTC2256 Alb CTLA4lg [13833-27669]
(5961 bp)

BC2259 FcRN inj frag
(16813 bp)

BC2258 B2M inj frag
(16075 bp)

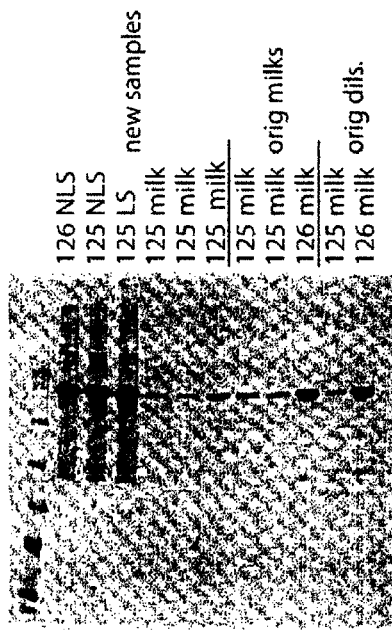

FcRn NB0094 p 55

1. MW
2. 126 non-lact serum
3. 125 non-lact serum
4. 125 lact serum
5. 125 milk d3
6. 125 milk d10
7. 125 fresh milk dil
8. 125 orig milk by vol
9. 125 orig milk by mass
10. 126 orig milk by mass
11. 125 orig milk sample
12. 126 orig milk sample All samples 4 ul 1:40 dilution
lanes 2-7 new samples
lanes 8-10 new dilutions of orig milk samples
lanes 11-12 orig milk samples
Licor scan

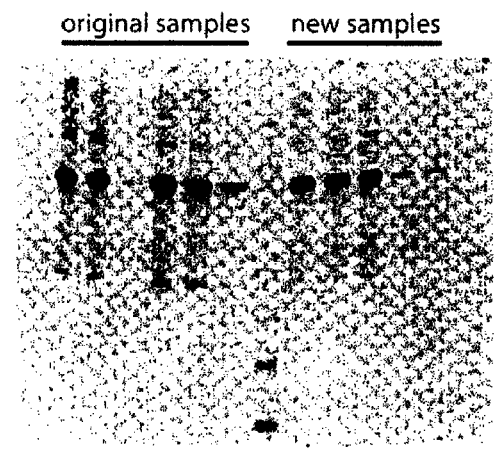

FcRn NB0094 p 54

1. 125 non-lact serum
2. 125 lact serum
3. 125 milk
4. 126 non-lact serum
5. 126 lact serum
6. 126 milk
7. MW
8. 126 non-lact serum
9. 125 non-lact serum
10. 125 lact serum
11. 125 milk d3
12. 125 fresh milk dil lanes 1-6: original samples
lanes 8-12: new samples All samples 4 ul 1:40 dilution
Licor scan

Fig. 5

NON-HUMAN TRANSGENIC MAMMAL EXPRESSING A HUMAN FCRN ON ITS MAMMARY GLAND CELLS AND EXPRESSING A TRANSGENIC PROTEIN-HUMAN FC-DOMAIN FUSION

RELATED APPLICATIONS

This application claims priority under 35 U.S.C. §119 from U.S. provisional application Ser. No. 60/745,287, filed Apr. 21, 2006. The entire contents of which is herein incorporated by reference.

FIELD OF THE INVENTION

The present invention relates, in part, to the field of protein production including products and methods for and related to protein production.

BACKGROUND OF THE INVENTION

Recombinant proteins provide effective therapies for many life-threatening diseases. The use of high expression level systems such as bacterial, yeast and insect cells for production of therapeutic proteins is mostly limited to small proteins without extensive post-translational modifications. Mammalian cell systems, can be used to produce proteins with many of the needed post-translational modifications, but can be more expensive due to the sophisticated culture systems that are, at times, required. Many of the limitations of mammalian cell culture systems have been overcome with the expression of recombinant proteins in the milk of transgenic mammals. Proteins have been produced in mammary glands of various transgenic animals with expression levels suitable for cost effective production at the scale of hundreds of kilograms of protein per year.

SUMMARY OF THE INVENTION

Provided herein are methods of expressing molecules, such as proteins, with, in some embodiments, post-translational modifications. The molecules can be produced in various tissues or cells of the body followed by translocation from the blood into the mammary gland through transport receptors, such as FcRn.

In one aspect, a non-human mammal that expresses a transport receptor, such as functional FcRn, in the mammary gland during lactation and a molecule, such as a transgenic protein, in the blood is provided. In one embodiment, the transport receptor is FcRn, pIgA-R or Tf receptor. In another embodiment, the non-human mammal comprises a transgenic nucleic acid encoding a transport receptor, such as FcRn, pIgA-R or Tf receptor, and a transgenic nucleic acid encoding a transgenic protein.

In another embodiment, when the transport receptor is FcRn, the non-human mammal also comprises a transgenic nucleic acid encoding beta-2 microglobulin. In still another embodiment, the transgenic nucleic acid encoding FcRn also encodes beta-2 microglobulin. In yet another embodiment, the non-human mammal comprises a transgenic nucleic acid that encodes FcRn and a transgenic nucleic acid that encodes beta-2 microglobulin that is separate from the transgenic nucleic acid that encodes FcRn.

In a further embodiment, the transgenic nucleic acid encoding a transport receptor also encodes a mammary gland-specific promoter (and is under the control of the mammary gland-specific promoter). In one embodiment, the mammary gland-specific promoter is a casein, lactoglobulin, whey acid promoter or lactalbumin promoter. In another embodiment, the transgenic nucleic acid encoding a transgenic protein also encodes a promoter that is its natural promoter (i.e., the promoter that controls its transcription as it occurs in nature without human intervention). In still another embodiment, the transgenic nucleic acid encoding a transgenic protein also encodes a non-mammary gland-specific promoter (and is under the control of the non-mammary gland-specific promoter). In one embodiment, the non-mammary gland-specific promoter is a non-mammary gland tissue-specific promoter, such as a liver-specific promoter. In another embodiment, the liver-specific promoter is an albumin promoter, mouse thyretin promoter (mTTR), endogenous human factor VIII promoter (F8) or human alpha-1-antitrypsin promoter (hAAT). In a further embodiment, the albumin promoter is human serum albumin (HSA) promoter, human albumin minimal promoter or mouse albumin promoter.

In one embodiment, the transgenic protein binds the transport receptor and is transported into the mammary gland through such interaction. In another embodiment, the transgenic protein that binds the transport receptor is a protein that naturally can bind the transport receptor and be transported into the mammary gland through such interaction (i.e., can bind the transport receptor in its native state without modification; comprises within its native structure a transport receptor-binding domain). In a further embodiment, the transgenic protein is fused to a transport receptor-binding domain and binds the transport receptor via the transport receptor-binding domain it is fused to. In one embodiment, the transport receptor-binding domain is transferrin or an IgA, IgG or IgM molecule or a portion thereof, such as a Fc-domain thereof.

In another embodiment, the transport receptor is FcRn, and the transgenic protein comprises an IgG molecule or a Fc-domain that binds FcRn. In a further embodiment, the transgenic protein is fused to an IgG molecule or a Fc-domain and binds the functional FcRn via the IgG molecule or Fc-domain. In a further embodiment, the IgG molecule or Fc-domain is a human IgG molecule or Fc-domain. In still a further embodiment, the Fc-domain is a Fc-domain of an IgG molecule. In yet a further embodiment, the Fc-domain is a Fc-domain of human IgG.

In another embodiment, the transgenic protein is a human protein. In still another embodiment, the transgenic protein is a therapeutic protein. In a further embodiment, the therapeutic protein is a human therapeutic protein.

In one embodiment, the transgenic protein is an antibody. In another embodiment, the antibody is an IgA, IgM or IgG antibody. In still another embodiment, the antibody is monoclonal or polyclonal. In a further embodiment, the antibody is a humanized antibody. In still another embodiment, the antibody is a human antibody. In yet a further embodiment, the antibody is a chimeric antibody.

In a another embodiment, the non-human mammal is a ruminant. In one embodiment, the ruminant is a cow, sheep, camel or goat. In a further embodiment, the ruminant is a goat.

In another aspect, a composition comprising milk obtained from any of the non-human mammals provided herein is provided. In one embodiment, the milk is not obtained from the non-human mammal prior to parturition. In another embodiment, the milk is obtained after parturition. In still another embodiment, the milk is obtained after and before parturition.

In still another aspect, a method for obtaining a transgenic protein, comprising collecting milk from any of the non-human mammals provided herein is provided. In one embodiment, the method further comprises separating the transgenic protein from the milk.

In a further aspect, a method for obtaining a transgenic protein present in the milk of a non-human mammal (e.g., any of the non-human mammals provided herein) is provided. In one embodiment, the method comprises generating a non-human mammal that expresses a transport receptor, such as functional FcRn, in the mammary gland during lactation and a molecule, such as a transgenic protein, in the blood.

In one embodiment, the transgenic protein binds a transport receptor, such as functional FcRn, and is transported into the mammary gland. In another embodiment, the method further comprises collecting milk from the non-human mammal. In another embodiment, the method further comprises purifying the transgenic protein from the milk.

In one aspect, any of the methods provided can comprise introducing into a non-human mammal a construct comprising a sequence encoding a transport receptor, such as FcRn, linked to a promoter which directs its expression in mammary cells, and a second construct comprising a sequence encoding a protein of interest. In one embodiment, the non-human mammal is created that comprises a transgenic nucleic acid encoding a transport receptor under the control of a mammary gland-specific promoter and a transgenic nucleic acid encoding a protein of interest under the control of a non-mammary gland-specific promoter.

In another embodiment, when the transport receptor is FcRn, the transgenic nucleic acid encoding FcRn can also encode beta-2 microglobulin. In yet another embodiment, the transgenic nucleic acid encoding beta-2 microglobulin is separate from the transgenic nucleic acid that encodes FcRn.

In a further embodiment, the transgenic nucleic acid encoding a transport receptor also encodes a mammary gland-specific promoter (and is under the control of the mammary gland-specific promoter). In one embodiment, the mammary gland-specific promoter is a casein, lactoglobulin, whey acid promoter or lactalbumin promoter. In another embodiment, the transgenic nucleic acid encoding a transgenic protein also encodes a promoter that is its natural promoter (i.e., the promoter that controls its transcription as it occurs in nature without human intervention). In another embodiment, the transgenic nucleic acid encoding a transgenic protein also encodes a non-mammary gland-specific promoter (and is under the control of the non-mammary gland-specific promoter). In one embodiment, the non-mammary gland-specific promoter is a non-mammary gland tissue-specific promoter, such as a liver-specific promoter. In another embodiment, the liver-specific promoter is an albumin promoter, mouse thyretin promoter (mTTR), endogenous human factor VIII promoter (F8) or human alpha-1-antitrypsin promoter (hAAT). In a further embodiment, the albumin promoter is human serum albumin (HSA) promoter, human albumin minimal promoter or mouse albumin promoter. In still a further embodiment, a transgenic nucleic acid encoding beta-2 microglobulin also encodes a mammary gland-specific promoter (and is under the control of the mammary gland-specific promoter).

In one embodiment, the level of the transgenic protein in the milk of the non-human mammal is increased compared to a non-human mammal of the same species that does not express the transgenic transport receptor, such as functional FcRn, in the mammary gland during lactation. In another embodiment, the level of the transgenic protein in the milk of the non-human mammal is increased compared to a non-human mammal of the same species that does not comprise a transgenic nucleic acid encoding the transport receptor, such as functional FcRn, under the control of a mammary gland-specific promoter.

In a further embodiment, the post-translation modifications (e.g., the glycosylation pattern) of the transgenic protein is different from the post-translation modifications (e.g., the glycosylation pattern) of the protein when expressed in the mammary gland of the non-human mammal. In one embodiment, the transgenic protein has an increased level of sialation. In another embodiment, the transgenic protein is fully sialated. In a further embodiment, the transgenic protein has an increased level of gamma-carboxylation.

In one embodiment, the transgenic protein binds the transport receptor and is transported into the mammary gland through such interaction. In another embodiment, the transgenic protein that binds the transport receptor is a protein that naturally can bind the transport receptor and be transported into the mammary gland through such interaction (i.e., can bind the transport receptor in its native state without modification; comprises within its native structure a transport receptor-binding domain). In a further embodiment, the transgenic protein is fused to a transport receptor-binding domain and binds the transport receptor via the transport receptor-binding domain it is fused to. In one embodiment, the transport receptor-binding domain is transferrin or an IgA, IgG or IgM molecule or a portion thereof, such as a Fc-domain thereof.

In another embodiment, the transport receptor is FcRn, and the transgenic protein comprises an IgG molecule or a Fc-domain that binds FcRn. In a further embodiment, the transgenic protein is fused to an IgG molecule or a Fc-domain and binds the functional FcRn via the IgG molecule or Fc-domain. In a further embodiment, the IgG molecule or Fc-domain is a human IgG molecule or Fc-domain. In still a further embodiment, the Fc-domain is a Fc-domain of an IgG molecule. In yet a further embodiment, the Fc-domain is a Fc-domain of human IgG.

In another embodiment, the transgenic protein is a human protein. In still another embodiment, the transgenic protein is a therapeutic protein. In a further embodiment, the therapeutic protein is a human therapeutic protein.

In one embodiment, the transgenic protein is an antibody. In another embodiment, the antibody is an IgA, IgG or IgM antibody. In still another embodiment, the antibody is monoclonal or polyclonal. In a further embodiment, the antibody is a humanized antibody. In still another embodiment, the antibody is a human antibody. In yet a further embodiment, the antibody is a chimeric antibody.

In a another embodiment, the non-human mammal is a ruminant. In one embodiment, the ruminant is a cow, sheep, camel or goat. In a further embodiment, the ruminant is a goat.

In a further aspect, a composition comprising the collected milk of any of the methods provided herein are provided. In one embodiment, the milk is not collected from the non-human mammal prior to parturition. In another embodiment, the milk is obtained after parturition. In still another embodiment, the milk is obtained after and before parturition.

In another aspect, a composition comprising milk from a non-human mammal, wherein the milk contains a transgenic protein that binds a transport receptor, such as functional FcRn, and wherein the transgenic protein is not expressed in the mammary gland at a level sufficient for protein production (e.g., not expressed at all or at very low levels) of the non-human mammal is provided. In one embodiment, the post-translation modifications (e.g., the glycosylation pattern) of the transgenic protein is different from the post-translation modifications (e.g., the glycosylation pattern) of the protein when expressed in the mammary gland of the non-human mammal. In another embodiment, the transgenic protein has an increased level of sialation. In one embodiment, the transgenic protein is fully sialated. In another embodiment, the transgenic protein has an increased level of gamma-carboxylation.

In one embodiment, the transgenic protein binds the transport receptor and is transported into the mammary gland through such interaction. In another embodiment, the transgenic protein that binds the transport receptor is a protein that naturally can bind the transport receptor and be transported into the mammary gland through such interaction (i.e., can bind the transport receptor in its native state without modification; comprises within its native structure a transport receptor-binding domain). In a further embodiment, the transgenic protein is fused to a transport receptor-binding domain and binds the transport receptor via the transport receptor-binding domain it is fused to. In one embodiment, the transport receptor-binding domain is transferrin or an IgA, IgG or IgM molecule or a portion thereof, such as a Fc-domain thereof.

In another embodiment, the transport receptor is FcRn, and the transgenic protein comprises an IgG molecule or a Fc-domain that binds FcRn. In a further embodiment, the transgenic protein is fused to an IgG molecule or a Fc-domain and binds the functional FcRn via the IgG molecule or Fc-domain. In a further embodiment, the IgG molecule or Fc-domain is a human IgG molecule or Fc-domain. In still a further embodiment, the Fc-domain is a Fc-domain of an IgG molecule. In yet a further embodiment, the Fc-domain is a Fc-domain of human IgG.

In another embodiment, the transgenic protein is a human protein. In still another embodiment, the transgenic protein is a therapeutic protein. In a further embodiment, the therapeutic protein is a human therapeutic protein.

In one embodiment, the transgenic protein is an antibody. In another embodiment, the antibody is an IgA, IgG or IgM antibody. In still another embodiment, the antibody is monoclonal or polyclonal. In a further embodiment, the antibody is a humanized antibody. In still another embodiment, the antibody is a human antibody. In yet a further embodiment, the antibody is a chimeric antibody.

In a another embodiment, the non-human mammal is a ruminant. In one embodiment, the ruminant is a cow, sheep, camel or goat. In a further embodiment, the ruminant is a goat.

In still another embodiment, the milk of any of the compositions provided is not milk obtained from the non-human mammal prior to parturition. In another embodiment, the milk is obtained after parturition. In still another embodiment, the milk is obtained after and before parturition.

Each of the limitations of the invention can encompass various embodiments of the invention. It, therefore, is anticipated that each of the limitations of the invention involving any one element or combinations of elements can be included in each aspect of the invention. These and other aspects of the invention will be described in further detail in connection with the detailed description of the invention.

BRIEF DESCRIPTION OF THE DRAWINGS

FIG. 5 shows the level of CTLA4IgG4 in the milk of lactating mice.

DETAILED DESCRIPTION OF THE INVENTION

Figure 1:
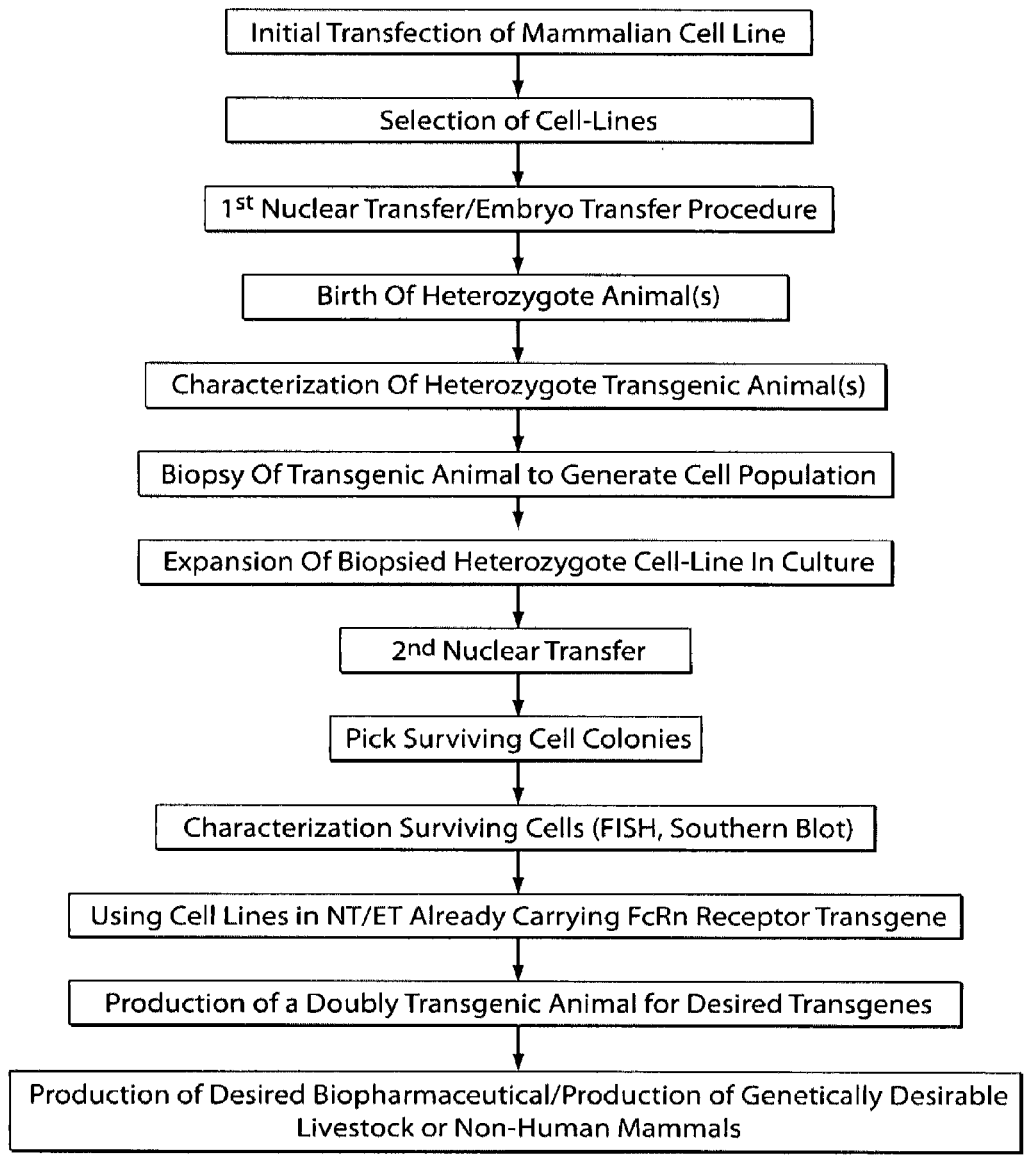
FIG. 1 shows a flowchart of a method for producing a transgenic animal.
Figure 2:
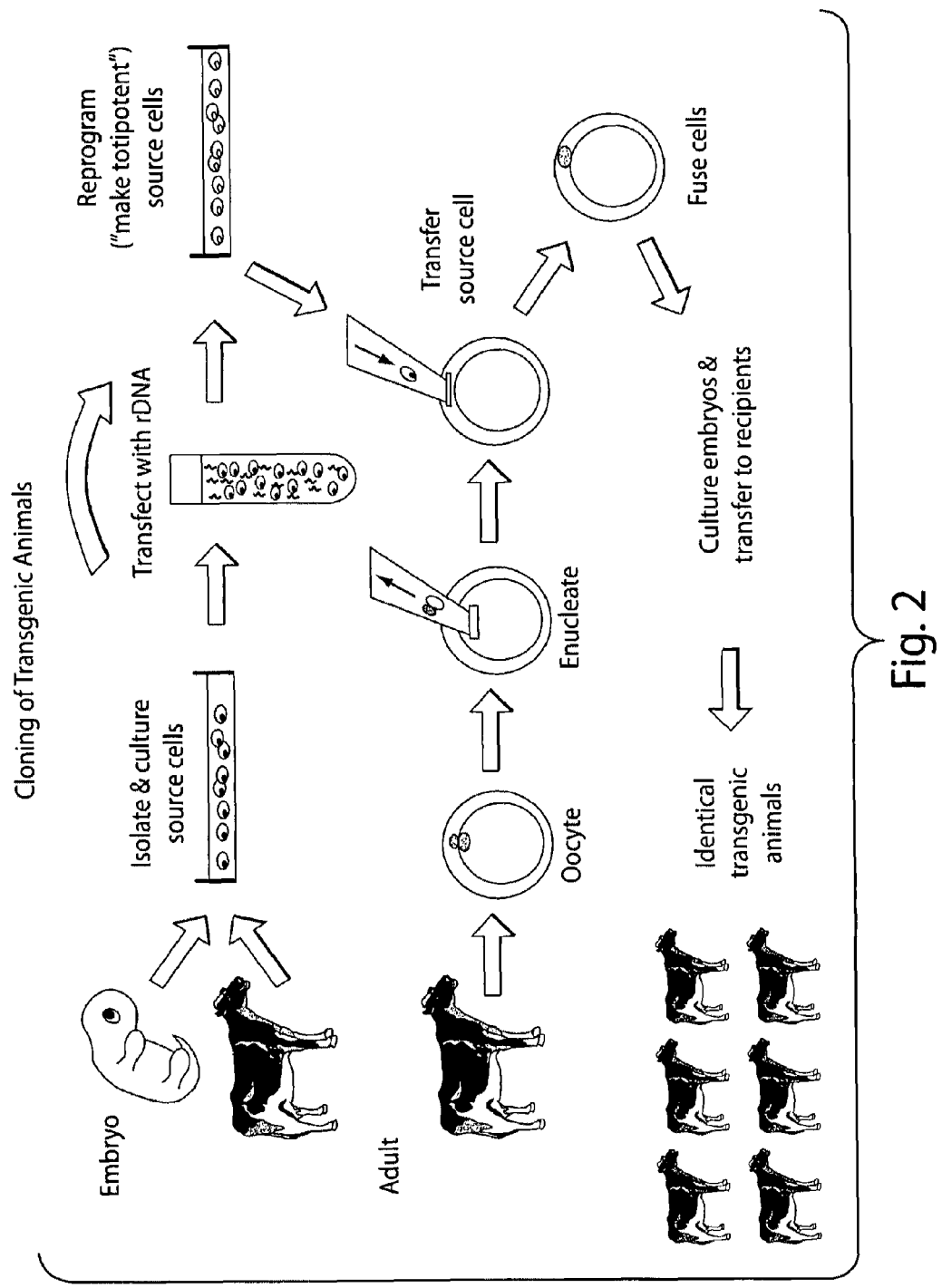
FIG. 2 shows a generalized diagram of a process for creating cloned animals.

The major function of the mammary gland is to produce proteins. The mammary gland is capable of producing milk that carries over 40 g/L of protein. By utilizing mammary gland-specific promoters to express proteins, the cellular machinery is capable of secreting high levels of properly folded proteins, such as antibodies. Proteins expressed in the mammary gland, however, may not be efficiently glycosylated or exhibit desired glycosylation patterns.

Incomplete glycosylation in the mammary gland can be a limitation for the production of certain proteins in the mammary gland. For instance, incomplete sialation of glycoproteins, as occurs when proteins are expressed in the mammary gland, has limited the efficacy of some protein products due to their more rapid clearance when used as a therapeutic protein. In particular, those proteins in which the glycosylation residues are exposed are more rapidly cleared by the asialo receptor in the liver. However, glycoproteins expressed in serum or blood are generally fully sialated. In addition, certain glyosylation events, such as gamma carboxylation, do not occur, or occur ineffectively, when a protein is expressed in the mammary gland. Therefore, methods have been devised to use the machinery of the mammary gland for secretion of proteins with desired glycosylation. In one aspect, methods are provided to produce a protein of interest in the serum of a non-human mammal, with a desired glycosylation pattern, and transport of the protein to the mammary gland resulting in the secretion of the protein in the milk of the non-human mammal. Transferring proteins of interest out of the circulating blood stream to the mammary gland allows for more convenient harvesting of the protein, as it is easier to milk the animal as opposed to bleeding it on a regular basis.

The methods provided, in some embodiments, employ expressing a transport receptor on cells of the mammary gland during lactation as well as a target protein that is bound and transported by the transport receptor. The protein that binds the transport receptor is expressed in tissues other than or in addition to the mammary gland and subsequently enters the blood and comes in contact with the transport receptor. When the transport receptor binds the target protein, the protein is then transported into the mammary gland and is secreted in milk.

As used herein, the "transport receptor" is any protein expressed in the mammary gland that can transport proteins into milk. Transport receptors, therefore, include pIgA-R, Tf receptor and neonatal Fc receptor (FcRn). The transport receptor, in one embodiment, is FcRn. It is known that FcRn plays an important role in regulating the serum half-lives of IgG antibodies when moving them into the systems of infants. FcRn is found on the endothelial cell walls and is responsible for the binding and recycling antibodies. This process involves binding and internalizing the antibody, followed by secretion of the antibody back into the plasma. In ruminants, this receptor is selectively expressed in mammary tissue just prior to parturition and transports antibodies from the serum into the mammary gland for colostrum. As lactation proceeds, this receptor is no longer expressed, and the level of antibody in the milk decreases significantly. In fact, the ruminant has a high level of FcRn in the mammary gland prior to parturition, which decreases following the birth of the young (Mayer, B. Immunology 2002 107 288-296), and the FcRn receptor in live stock is thought to actively transport antibodies into the milk (Kacskovics, Vet Immunology and Immunopathology, 1202 (2004) 351-362). Thus, one function of FcRn is to pull antibody into the mammary gland for colostrum.

With the methods provided herein, transport receptors, such as FcRn, can be expressed continuously throughout lactation. Transport receptors, such as FcRn, can facilitate the transport of proteins that bind to them into the mammary gland.

FcRn sequences are known and include the sequences for the FcRn of ruminants, such as cow, dromedary and sheep. Such sequences are provided in PCT Publication WO 01/57088 and are incorporated herein by reference. The FcRn can, in one embodiment, be human FcRn. The sequence of human FcRn is provided as NCBI Accession number NM_004107 and is also expressly incorporated herein by reference. Sequences for other transport receptors are also known in the art.

The transport receptor (e.g., FcRn) is expressed in the mammary gland of a non-human mammal in such a way so that it is functional. As used herein, "functional" is meant to refer to a transport receptor that is able to bind a protein in the blood and transport it into a mammary cell so that it is secreted in milk.

To be a functional FcRn, the FcRn combines with beta-2 microglobulin. As used herein, the term "functional FcRn" is meant to refer to FcRn when combined with beta-2 microglobulin. The term "FcRn" is meant to refer to either functional FcRn or its subunit that combines with beta-2 microglobulin (e.g., the FcRn alpha chain). Beta-2 microglobulin can be endogenously expressed or it can be transgenically expressed along with FcRn in the mammary gland of a non-human mammal. In one embodiment, when the beta-2 microglobulin is endogenous, its expression is increased such that it is produced in sufficient quantities to combine to form a functional FcRn and to result in the transport of a molecule, such as a protein, into milk. Methods for controlling endogenous expression of beta-2 microglobulin will be apparent to one of ordinary skill in the art.

The methods provided allow for any protein of interest (including peptide fragments thereof; preferably, in some embodiments, biologically active peptide fragments thereof)) in the blood to be transported into the milk of a non-human mammal. The protein can be any protein that binds to a transport receptor. The protein, therefore, can be one that binds functional FcRn. In one embodiment, the protein comprises a domain that binds the transport receptor. Such a domain can be any portion of the protein (or other molecule) that can bind the transport receptor and result in its transport into the mammary gland and secretion into milk. The protein of interest can, therefore, be one that naturally can bind the transport receptor and be transported into the mammary gland and secreted into milk, e.g., transferrin or an antibody, such as an IgA, IgM or IgG antibody. Fragments of these proteins that bind a transport receptor and be transported into the mammary gland and secreted into milk can also be a protein of interest.

In other embodiments, the protein of interest that binds a transport receptor can be fused to a transport receptor-binding domain or a protein (or other molecule) that comprises such a domain, and its binding to the transport receptor occurs via the transport receptor-binding domain or protein (or other molecule) that comprises such a domain. Therefore, proteins of interest can be fused to proteins that can bind a transport receptor (e.g., transferrin or an antibody, such as an IgA, IgM or IgG antibody) or to a portion of these proteins that can bind a transport receptor (e.g., a Fc-domain, such as IgG Fc-domain). The transport receptor-binding domain, in some embodiments, is a Fc-domain, such as an IgG Fc-domain. In other embodiment, the IgG Fc-domain is a human IgG Fc-domain.

While the description provided focuses on the transport of proteins via a transport receptor, other molecules can also be transported into the mammary cells by coupling them to a domain that binds a transport receptor or a protein (or other molecule) that comprises such a domain, such those described above. In some embodiments, these other molecules are nucleic acids, small molecules, such as drugs, etc. In one embodiment, therefore, the invention provides a method for gene therapy on the mammary gland. With the methods provided, nucleic acid vectors that are bound to a transport receptor-binding domain or a protein (or other molecule) that comprises such a domain are delivered from the blood into the basal surface of the mammary gland. In one embodiment, therefore, a non-human mammal that expresses a transport receptor (endogenously or transgenically) and a nucleic acid or other molecule fused to a domain that binds a transport receptor or a protein (or other molecule) that comprises such a domain is provided. Methods for producing such a non-human mammal are also provided. In one embodiment, the non-human mammal that expresses a transport receptor in the mammary gland can express or be engineered to express a nucleic acid fused to a domain that binds a transport receptor or a protein (or other molecule) that comprises such a domain. In another embodiment, the non-human mammal is engineered to express the transport receptor in addition to the nucleic acid fused to a domain that binds a transport receptor or a protein (or other molecule) that comprises such a domain. Methods for engineering such expression are as provided elsewhere herein.

The term "antibody" refers to a protein comprising at least one, and preferably two, heavy (H) chain variable regions (abbreviated herein as VH), at least one and preferably two light (L) chain variable regions (abbreviated herein as VL), and at least one, preferably two heavy chain constant regions. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (See, e.g., Kabat, E. A., et al. (1991) Sequences of Proteins of Immunological Interest, Fifth Edition, U.S. Department of Health and Human Services, NIH Publication No. 91-3242, and Chothia, C. et al. (1987) J. MOL. BIOL. 196:901-17, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The antibody can further include a hinge region. As used herein, an "assembled" antibody is an antibody in which the heavy chains are associated with each other, e.g., interconnected by disulfide bonds. Each heavy chain hinge region includes at least one, and often several, cysteine residues. In the assembled antibody, the cysteine residues in the heavy chains are aligned so that disulfide bonds can be formed between the cysteine residues in the hinge regions covalently bonding the two heavy-light chain heterodimers together. Thus, fully assembled antibodies are bivalent in that they have two antigen binding sites. The term "antibody" (or "immunoglobulin") as used herein, also refers to antigen-binding fragments of a full-length antibody, such as, e.g., a F(ab')2 fragment, a bivalent fragment comprising two Fab fragments linked by a disulfide bridge at the hinge region. Antibody fragments are obtained using conventional techniques known to those with skill in the art and can be screened for utility in the same manner as intact antibodies.

The basic antibody is made up of two identical light chains and two identical heavy chains. Structurally, these polypeptide chains can be divided into loops or domains of about 110 amino acids bridged by disulfide bonds. This structural motif is characteristic of members of the immunoglobulin superfamily, which includes various cell adhesion molecules (CAMs), CD4, CD8, CD28, and members of the B7 family of co-stimulatory molecules. Members of this superfamily can be the protein that is expressed in the blood and is subsequently secreted in milk as described herein. Light chains have two domains and heavy chains have four or five domains. The domains at the amino ends of heavy and light chains have a highly variable amino acid sequence and are called V domains. The other domains have a relatively constant sequence and are called C domains. Each light chain is paired by disulfide bonds to a heavy chain so that their two V domains come together to form the antigen-binding site. The amino acid sequence variability within the V domains is actually focused in three hypervariable regions.

An "antigen-binding fragment" of an antibody refers to one or more portions of an antibody that retain the ability to specifically bind to an antigen. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies. In some embodiments, preferred antigen-binding fragments include a Fab fragment, a $F(ab')_2$ fragment, and a Fv fragment CDR3.

The antibody can be any antibody from any antibody class. As used herein, a "class" of antibodies refers to the five major isotypes of antibodies, including IgA, IgD, IgE, IgG, and IgM. A "subclass" of antibodies refers to the subclassification of a given class of antibodies based on amino acid differences among members of the class, e.g., the class of antibodies designated IgG can be divided into the subclasses of, e.g., IgG1, IgG2, IgG3 and IgG4, and the class of antibodies designated as IgA can be divided into the subclasses of IgA1 and IgA2.

In neonates, maternal milk contains both IgA and IgG. Once ingested, the IgG is taken up specifically in the gut of the neonate via IgG-specific FcRn. Thus, FcRn is involved in the transcytosis of maternal IgG antibodies from the apical to the basolateral surface of the gut epithelium. FcRn is also responsible for maternal IgG transport across the placenta. IgG is the most abundant isotype of antibody in the serum of human adults, constituting approximately 80% of the total serum immunoglobulin. IgG is a monomeric molecule having a tetrameric structure consisting of two A heavy immunoglobulin chains and two (P or Σ) light immunoglobulin chains. The heavy and light immunoglobulin chains are generally inter-connected by disulfide bonds. The antibody further includes a hinge region rich in proline residues, which confers segmental flexibility to the molecule. IgG demonstrates numerous biological functions, including agglutination of antigen, opsonization, antibody-dependent cell-mediated cytotoxicity, passage through the placenta, activation of complement, neutralization of toxins, immobilization of bacteria, and neutralization of viruses. In one embodiment, the antibody is an IgG antibody, e.g., an IgG1, IgG2, IgG3 or IgG4 antibody. In another embodiment, the antibody is an IgG4 antibody or antigen-binding fragment thereof.

In yet other embodiments, the antibodies can be chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that retains only the antigen-binding CDRs from the parent antibody in association with human framework regions (see, Waldmann, 1991, *Science* 252:1657). Such chimeric or humanized antibodies retaining binding specificity of the murine antibody are expected to have reduced immunogenicity when administered in vivo for diagnostic, prophylactic or therapeutic applications according to the invention.

As used herein, a "chimeric antibody heavy chain" refers to those antibody heavy chains having a portion of the antibody heavy chain, e.g., the variable region, at least 85%, preferably, 90%, 95%, 99% or more identical to a corresponding amino acid sequence in an antibody heavy chain from a particular species, or belonging to a particular antibody class or type, while the remaining segment of the antibody heavy chain (e.g., the constant region) being substantially identical to the corresponding amino acid sequence in another antibody molecule. For example, the heavy chain variable region has a sequence substantially identical to the heavy chain variable region of an antibody from one species (e.g., a "donor" antibody, e.g., a rodent antibody), while the constant region is substantially identical to the constant region of another species antibody (e.g., an "acceptor" antibody, e.g., a human antibody). The donor antibody can be an in vitro generated antibody, e.g., an antibody generated by phage display.

The term "humanized" or "CDR-grafted" light chain variable region refers to an antibody light chain comprising one or more CDR's, or having an amino acid sequence which differs by no more than 1 or 2 amino acid residues to corresponding one or more CDR's from one species, or antibody class or type, e.g., a "donor" antibody (e.g., a non-human (usually a mouse or rat) immunoglobulin, or an in vitro generated immunoglobulin); and a framework region having an amino acid sequence about 85% or higher, preferably 90%, 95%, 99% or higher identical to a corresponding part of an acceptor antibody framework from a different species, or antibody class or type, e.g., a naturally-occurring immunoglobulin framework (e.g., a human framework) or a consensus framework. In some embodiments, the framework region includes at least about 60, and more preferably about 70 amino acid residues identical to those in the acceptor antibody light chain variable region framework, e.g., a naturally-occurring antibody framework (e.g., a human framework) or a consensus framework. Humanization (also called Reshaping or CDR-grafting) is an established technique for reducing the immunogenicity of monoclonal antibodies from xenogeneic sources, such as mice. Humanized antibodies can be generated through standard molecular biology techniques. In one embodiment, the technique comprises grafting the rodent complementarity-determining regions (CDRS) into a human framework. However, this technique is mostly an iterative process and a number of elements come into play when designing a humanized antibody: the length of the CDRs, the human frameworks and the substitution of residues from the rodent mAb into the human framework regions (backmutations).

According to an alternative embodiment, the antibodies can be modified to be in the form of a bispecific antibody, or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multi specific antibody" is intended to include any agent, e.g., a protein, peptide, or protein or peptide complex, which has more than two different binding specificities which bind to, or interact with (a) a cell surface antigen, (b) an Fc receptor on the surface of an effector cell, and (c) at least one other component. Accordingly, the invention includes, but is not limited to, bispecific, trispecific, tetraspecific, and other multispecific antibodies which are directed to cell surface antigens, and to Fc receptors on effector cells. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

In certain embodiments, the antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse have been grafted onto human framework sequences (referred to herein as "humanized antibodies"). Human antibodies are generated using transgenic mice carrying parts of the human immune system rather than the mouse system.

In one embodiment, therefore, the milk of a transgenic non-human mammal can be enriched for antibodies. The antibodies can be monoclonal or polyclonal. Further, the antibodies can be human antibodies. The production of human antibodies in non-human animals is established. Mice have been developed that carry the human genomic sequences that go through maturation to give rise to fully human polyclonal antibodies in the blood stream. These animals become the source of monoclonal antibody clones that are fully human (Abgenix and Medarex). Humanization of antibodies has also been carried in a bovine system in which cattle carrying the human antibody genomic sequence have been generated. Following antigen stimulation, these sequences are capable of rearranging and producing human antibodies in the blood stream. While the level of these polyclonal human antibodies may be low in the blood stream, a transport receptor, such as the human FcRn expressed selectively in the mammary tissue, can bind these polyclonal antibodies and release them into the mammary gland. The invention therefore provides an enrichment system for human antibodies over background, such as the bovine background. By selectively binding the human antibody it is possible to drive the concentration in the mammary gland higher than what is found in the bloodstream. This is supported by studies that show that selective binding of human antibodies by the human FcRn (Ober et al., Inter Imm 13:1551-59 (2001)).

Any of the antibodies described herein, e.g., chimeric, humanized or human antibodies, can include further modifications to their sequence. e.g., the sequence can be modified by addition, deletion or substitution, e.g., a conservative substitution.

An antibody heavy chain can be modified using oligonucleotide mutagenesis. Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* USA, 75: 5765[1978]). In order to test the modified antibodies, in one embodiment, the mutagenized antibody sequence encoding the heavy and/or light chain are used to generate transgenic mice. Mice are then tested for expression of the antibody. Optionally, the antibody generated can be tested for specific activity. Such methods are known in the art.

The antibody, as well as any of the other proteins that can bind the transport receptor and be secreted in milk according to the methods provided herein, are in some embodiments heterologous (or exogenous). "Heterologous" or "exogenous", as used herein, is intended to refer to proteins, such as antibodies, that are not endogenously produced in the mammal.

In other embodiments, the proteins are not normally produced in the mammary gland (e.g., a protein only present in serum) or is normally produced in the mammary gland but at a level lower than when the methods provided herein are employed. In other words, the methods provided herein, in some embodiments, result in an augmented or enhanced level of the protein in the mammary gland and/or in the milk as compared to the production of the protein in the same animal when a method provided herein is not employed (i.e., without the enhanced expression of the transport receptor).

The protein that binds a functional transport receptor, in some embodiments, is fused to a domain that binds the functional transport receptor or a protein (or other molecule) comprising such a domain. In such instances, the protein binds the functional transport receptor via the domain or protein (or other molecule) comprising the domain. For example, the domain that binds the transport receptor can be a Fc-domain that binds FcRn. In another embodiment, the Fc-domain is the Fc portion of an IgG antibody or fragment thereof. In one embodiment, the Fc-domain is a human Fc-domain. In another embodiment, the Fc-domain is human IgG Fc-domain, such as human IgG4 Fc-domain. In one embodiment, therefore, a platform for the production of fusion proteins (e.g., single chain fusion proteins) is provided. A fusion protein comprises a domain that binds a functional transport receptor (e.g., a Fc-domain) or a protein (or other molecule) that comprises such a domain (e.g., transferrin, IgA, IgG or IgM) and a protein of interest (which include peptide fragment thereof). For example, the Fc portion of IgG (for recognition by FcRn) can be fused to a biologically active CD4 protein, or a zymogen fragment of an otherwise biologically active molecule or fragment thereof, to make a protein that recognizes and binds to the Human Immunodeficiency Virus (HIV). This can be done by using the amino-terminal CD4 analogue that binds HIV and a recombinant Fc-domain.

Other protein fusions can include proteins or fragments thereof that have their therapeutic potential, including those with enhanced by post-translational processing in organs in the body other than in the mammary gland. Such proteins include myelin basic protein, insulin, CD55, urokinase, alpha-1-antitrypsin, protein C, angiotensinogen, antithrombin, apolipoprotein A-I, apolipoprotein A-II, apolipoprotein C-I, apolipoprotein C-II, apolipoprotein C-III, apolipoprotein E, atrial natriuretic factor, calcitonin, chorionic gonadotropin, complement C2, complement C3, complement C4, complement C9, corticotropin releasing factor, decorin, endothelin, epidermal growth factor, erythropoietin, C1 esterase inhibitor, factor VII, factor VIII, factor IX, factor X, Christmas factor, fibrinogen, gastrin releasing peptide, glucagon, alpha glucosidase, human growth hormone, hemopexin, inhibin, α-interferon, β-interferon, γ-interferon, IL-1, IL-2, IL-3, IL-12, kininogen, lactoferrin, the beta subunit of leuteinizing hormone, leuteinizing hormone, lymphotoxin, neurotensin, nerve growth factor, Platelet Derived Growth Factor, parathyroid hormone, tissue plasminogen activator, prolactin, proopiomelanocortin, protein C, prothrombin, relaxin, renin, somatostatin, tachykinin, transferrin, substance P, substance K, urokinase, butyl-cholinesterase, and soluble receptor protein (such as TNF alpha receptor, CTLA4, CD137 or any receptor on immunologically relevant cells), including recombinant human versions thereof.

In some embodiments, the protein that is transported from the blood to the mammary gland comprises post-translational modifications and/or exhibits a different glycosylation pattern than when the same protein is produced in the mammary gland of the same type of mammal. In some embodiments, the protein that is transported comprises post-translation modifications that are different than, or in addition to, post-translational modifications that occur when the same protein is produced in the mammary gland of the same type of mammal. In one embodiment, the transported proteins comprise post-translational modifications that are not produced if the proteins were expressed in the mammary gland. In some embodiments, the glycosylation pattern is that of a serum protein. In another embodiment, the transported protein exhibits an increased level of sialation as compared to the same protein when expressed in the mammary gland of the same type of mammal. In one embodiment, the transported protein is fully sialated. In still other embodiments, the transported protein has an increased level of gamma-carboxylation as compared to the same protein when expressed in the mammary gland of the same type of mammal.

As provided herein, the transport receptor and protein that binds the transport receptor can be expressed transgenically in a mammal. As used herein, a "transgenic mammal" is a mammal in which one or more, and preferably essentially all, of the cells of the animal contain a heterologous nucleic acid introduced by way of human intervention, such as by transgenic techniques known in the art. The present invention contemplates all manners known to those of skill in the art for introducing nucleic acids to generate transgenic animals. For example, methods of producing transgenic goats are known in the art. The transgene can be introduced into the germline of a goat by microinjection as described, for example, in Ebert et al. (1994) *Bio/Technology* 12:699. The method of which is hereby incorporated by reference. Techniques are also provided herein and are described in more detail below.

The term "transgene" means a nucleic acid sequence, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). A transgene can include one or more transcriptional regulatory sequences and any other nucleic acid, such as introns, that may be necessary for optimal expression and secretion of the selected nucleic acid encoding the protein of interest, e.g., in a mammary gland, all operably linked to the selected nucleic acid encoding the protein of interest, and may include an enhancer sequence and/or an insulator sequence. When such a nucleic acid encodes a protein that is to be transported from the blood to the mammary gland and/or milk, the nucleic acid sequence is operatively linked to a non-mammary gland-specific promoter, e.g., a promoter sequence that results in the expression of the protein in tissues other than or in addition to the mammary gland. Some of such promoters include any promoter that results in the presence of the transgenic protein in the blood stream. Such promoters include tissue-specific promoters that are not specific to the mammary gland that result in the production of the transgenic protein in a specific tissue and subsequent secretion of the transgenic protein into the blood. One of ordinary skill in the art is familiar with promoters that would be suitable for performing the methods provided and for producing the compositions described herein.

Examples of tissue-specific promoters include the immunoglobulin promoter described by Brinster et al., Nature, 306:332-336 (1983) and Storb et al., Nature, 310:238-231 (1984); the elastase-I promoter described by Swift et al., Cell, 38:639-646 (1984); the globin promoter described by Townes et al., Mol. Cell. Biol., 5:1977-1983 (1985), and Magram et al., Mol. Cell. Biol., 9:4581-4584 (1989), the insulin promoter described by Bucchini et al., Proc. Natl. Acad. Sci., USA, 83:2511-2515 (1986) and Edwards et al., Cell, 58:161 (1989); the immunoglobulin promoter described by Ruscon et al., Nature, 314:330-334 (1985) and Grossched et al., Cell, 38:647-658 (1984); the alpha actin promoter described by Shani, Mol. Cell. Biol., 6:2624-2631 (1986); the alpha crystalline promoter described by Overbeek et al., Proc. Natl. Acad. Sci. USA, 82:7815-7819 (1985); the prolactin promoter described by Crenshaw et al., Genes and Development, 3:959-972 (1989); the proopiomelanocortin promoter described by Tremblay et al., Proc. Natl. Acad. Sci., USA, 85:8890-8894 (1988); the beta thyroid stimulating hormone (BTSH) promoter described by Tatsumi et al., Nippon Rinsho, 47:2213-2220 (1989); the mouse mammary tumor virus (MMTV) promoter described by Muller et al., Cell, 54:105 (1988); the albumin promoter described by Palmiter et al., Ann. Rev. Genet., 20:465-499 (1986); the Keratin promoter described by Vassar et al., Proc. Natl. Acad. Sci., USA, 86:8565-8569 (1989); the osteonectin promoter described by McVey et al., J. Biol. Chem., 263:11,111-11,116 (1988); the prostate-specific promoter described by Allison et al., Mol. Cell. Biol., 9:2254-2257 (1989); the opsin promoter described by Nathans et al., Proc. Natl. Acad. Sci., USA, 81:4851-4855 (1984); the olfactory marker protein promoter described by Danciger et al., Proc. Natl. Acad. Sci., USA, 86:8565-8569 (1989); the neuron-specific enolase (NSE) promoter described by Forss-Pelter et al., J. Neurosci. Res., 16:141-151 (1986); the L-7 promoter described by Sutcliffe, Trends in Genetics, 3:73-76 (1987) and the protamine 1 promoter described Peschon et al., Ann. New York Acad. Sci., 564:186-197 (1989) and Braun et al., Genes and Development, 3:793-802 (1989). Examples of tissue-specific promoter with information regarding their tissue specificity can be found in U.S. Pat. No. 5,416,017, the contents pertaining to the promoters and their specificity are incorporated herein by reference. Other such promoters will be known to those of ordinary skill in the art.

In some embodiments, the non-mammary gland-specific promoter is a liver-specific promoter, such as an albumin promoter (e.g., the human serum albumin promoter). Other examples of liver-specific promoters include, but are not limited to, the mouse thyretin promoter (mTTR), the endogenous human factor VIII promoter (F8), human alpha-1-antitrypsin promoter (hAAT), human albumin minimal promoter and mouse albumin promoter. In one embodiment, the mTTR promoter is used. The mTTR promoter is described in R. H. Costa et al., 1986, Mol. Cell. Biol. 6:4697. The F8 promoter is described in Figueiredo and Brownlee, 1995, J. Biol. Chem. 270:11828 11838. Other liver-specific promoters will be known to those of ordinary skill in the art.

The non-mammary gland-specific promoter can also be the native promoter of the protein of interest (e.g., for CTLA4, the native CTLA4 promoter can be used) for expression in the natural organ (i.e., the organ that normally produces the protein). In some embodiments, the promoters can be B-cell-specific promoters. In one embodiment, when an antibody is the protein of interest the non-mammary gland-specific promoter is a B-cell-specific promoter.

Mammals are defined herein as all animals that have mammary glands and produce milk. Any non-human mammal can be utilized in the present invention. In some embodiments, the non-human mammals are ruminants, e.g., cows, sheep, camels or goats. In one embodiment, the non-human mammal is a goat. In other embodiments, the non-human mammals include oxen, horses, llamas, and pigs. In still other embodiments, the non-human mammals are not rodents (e.g., mice), because mice are believed to transport out of the milk into the blood.

Methods for generating non-human transgenic mammals can involve introducing DNA constructs into the germ line of a mammal to make a transgenic mammal. For example, one or several copies of the construct can be incorporated into the genome of a mammalian embryo by standard transgenic techniques. In addition, non-human transgenic mammals can be produced using a somatic cell as a donor cell. The genome of the somatic cell can then be inserted into an oocyte and the oocyte can be fused and activated to form a reconstructed embryo. For example, methods of producing transgenic animals using a somatic cell are described in PCT Publication WO 97/07669; Baguisi et al. NATURE BIOTECH., vol. 17 (1999), 456-461; Campbell et al., NATURE, vol. 380 (1996), 64-66; Cibelli et al., SCIENCE, vol. 280 (1998); Kato et al., SCIENCE, vol. 282 (1998), 2095-2098; Schnieke et al., SCIENCE, vol. 278. (1997), 2130-2133; Wakayama et al., NATURE, vol. 394 (1998), 369-374; Well et al., BIOL. REPROD., vol. 57 (1997): 385-393.

In one embodiment, a non-human mammal of the invention has at least two exogenous nucleic acids inserted into its genome. The first nucleic acid encodes a transport receptor (e.g., FcRn), while the second nucleic acid encodes a protein of interest. When the transport receptor is FcRn, the nucleic acid can, in some embodiments, additionally encode beta-2 microglobulin. In other embodiments the beta-2 microglobulin can be encoded by a nucleic acid separate from the nucleic acid that encodes FcRn (e.g., FcRn alpha chain). The aforementioned nucleic acids can further encode a promoter that results in expression of the transport protein in the mammary gland of the transgenic non-human mammal (i.e., a promoter activated during the milk production cycle that can be used to result in the expression of the transport receptor in the mammary gland). For example, such a promoter can be a mammary gland-specific promoter.

A cassette which encodes a protein can be assembled as a construct which includes a promoter for a specific tissue. The construct can also include a 3' untranslated region downstream of the DNA sequence coding for the protein. Such regions can stabilize the RNA transcript of the expression system and thus increases the yield of desired protein from the expression system. Among the 3' untranslated regions useful in the constructs for use in the invention are sequences that provide a poly A signal. Such sequences may be derived, e.g., from the SV40 small t antigen or bgh bovine growth hormone, the casein 3' untranslated region or other 3' untranslated sequences well known in the art. In one aspect, the 3' untranslated region is derived from a milk specific protein. The length of the 3' untranslated region is not critical but the stabilizing effect of its poly A transcript appears important in stabilizing the RNA of the expression sequence.

Optionally, the construct can include a 5' untranslated region between the promoter and the DNA sequence encoding the signal sequence. Such untranslated regions can be from the same control region from which promoter is taken or can be from a different gene, e.g., they may be derived from other synthetic, semi-synthetic or natural sources. Again their specific length is not critical, however, they can be useful in improving the level of expression. The construct can, in some embodiments, also include about 10%, 20%, 30%, or more of the N-terminal coding region of a gene preferentially expressed in mammary epithelial cells, such as when making a fusion protein.

In some embodiments, when the protein is an antibody, the nucleic acid encoding the antibody can be polycistronic, e.g., the heavy chain coding sequence and the light chain coding sequence can have an internal ribosome entry site (IRES) between them.

The construct can be prepared using methods known in the art. The construct can be prepared as part of a larger plasmid. Such preparation allows the cloning and selection of the correct constructions in an efficient manner. The construct can be located between convenient restriction sites on the plasmid so that they can be easily isolated from the remaining plasmid sequences for incorporation into the desired mammal.

The DNA constructs used to make a transgenic mammal can include at least one insulator sequence. The terms "insulator", "insulator sequence" and "insulator element" are used interchangeably herein. An insulator element is a control element which insulates the transcription of genes placed within its range of action but which does not perturb gene expression, either negatively or positively. Preferably, an insulator sequence is inserted on either side of the DNA sequence to be transcribed. For example, the insulator can be positioned about 200 bp to about 1 kb, 5' from the promoter, and at least about 1 kb to 5 kb from the promoter, at the 3' end of the gene of interest. The distance of the insulator sequence from the promoter and the 3' end of the gene of interest can be determined by those skilled in the art, depending on the relative sizes of the gene of interest, the promoter and the enhancer used in the construct. In addition, more than one insulator sequence can be positioned 5' from the promoter or at the 3' end of the transgene. For example, two or more insulator sequences can be positioned 5' from the promoter. The insulator or insulators at the 3' end of the transgene can be positioned at the 3' end of the gene of interest, or at the 3'end of a 3' regulatory sequence, e.g., a 3' untranslated region (UTR) or a 3' flanking sequence. One example of an insulator is a DNA segment which encompasses the 5' end of the chicken β-globin locus and corresponds to the chicken 5' constitutive hypersensitive site as described in PCT Publication 94/23046, the contents of which are incorporated herein by reference.

Suitable methods for transforming or transfecting host cells can be found in Sambrook et al., *Molecular Cloning: A Laboratory Manual, 2$^{nd}$ ed., Cold Spring Harbor Laboratory*, (Cold Spring Harbor Laboratory Press, Cold Spring Harbor, N.Y., 1989), and other suitable laboratory manuals. Two useful approaches are electroporation and lipofection. Brief examples of each are described below.

The DNA construct can be stably introduced into a donor cell line by electroporation using the following protocol: somatic cells, e.g., fibroblasts, such as embryonic fibroblasts, are re-suspended in PBS at about $4\times10^6$ cells/ml. Fifty micrograms of linearized DNA are added to the 0.5 ml cell suspension, and the suspension is placed in a 0.4 cm electrode gap cuvette (Biorad). Electroporation is performed using a Biorad Gene Pulser electroporator with a 330 volt pulse at 25 mA, 1000 microFarad and infinite resistance. If the DNA construct contains a Neomyocin resistance gene for selection, neomyocin resistant clones are selected following incubation with 350 microgram/ml of G418 (GibcoBRL) for 15 days.

The DNA construct can be stably introduced into a donor somatic cell line by lipofection using a protocol such as the following: about $2\times10^5$ cells are plated into a 3.5 cm diameter well and transfected with 2 micrograms of linearized DNA using LipfectAMINE™ (GibcoBRL). Forty-eight hours after transfection, the cells are split 1:1000 and 1:5000 and, if the DNA construct contains a neomyosin resistance gene for selection, G418 is added to a final concentration of 0.35 mg/ml. Neomyocin resistant clones are isolated and expanded for cryopreservation as well as nuclear transfer. In addition, biological vectors, e.g., viral vectors can be used to introduce DNA into cells.

Useful transcriptional promoters for expression of a functional transport receptor include any promoter that is activated in mammary epithelial cells of any species. Such promoters include promoters that are mammary gland-specific (i.e., are preferentially activated in mammary cells). Mammary gland-specific promoters include the promoters that control the genes encoding milk proteins such as caseins, lactoglobulin (e.g., beta lactoglobulin (Clark et al., (1989) BIO/TECHNOLOGY 7: 487-492)), whey acid protein (Gordon et al. (1987) BIO/TECHNOLOGY 5: 1183-1187), and lactalbumin (Soulier et al., (1992) FEBS Letts. 297: 13). Casein promoters may be derived from the alpha, beta, gamma or kappa casein genes of any mammalian species; in some embodiments, a preferred promoter, in some embodiments, is derived from the goat beta casein gene (DiTullio, (1992) BIO/TECHNOLOGY 10:74-77). The promoter can also be from lactoferrin or butyrophin. Any of the promoters described herein can be derived from cDNA or genomic sequences. In some embodiments, they are genomic in origin.

DNA sequence information is available for the mammary gland-specific genes listed above, in at least one, and often in several organisms. See, e.g., Richards et al., J. BIOL. CHEM. 256, 526-532 (1981) (α-lactalbumin rat); Campbell et al., NUCLEIC ACIDS RES. 12, 8685-8697 (1984) (rat WAP); Jones et al., J. BIOL. CHEM. 260, 7042-7050 (1985) (rat β-casein); Yu-Lee & Rosen, J. BIOL. CHEM. 258, 10794-10804 (1983) (rat γ-casein); Hall, BIOCHEM. J. 242, 735-742 (1987) (α-lactalbumin human); Stewart, NUCLEIC ACIDS RES. 12, 389 (1984) (bovine αs1 and κ casein cDNAs); Gorodetsky et al., GENE 66, 87-96 (1988) (bovine β casein); Alexander et al., EUR. J. BIOCHEM. 178, 395-401 (1988) (bovine κ casein); Brignon et al., FEBS LETT. 188, 48-55 (1977) (bovine αs2 casein); Jamieson et al., GENE 61, 85-90 (1987), Ivanov et al., BIOL. CHEM. Hoppe-Seyler 369, 425-429 (1988), Alexander et al., NUCLEIC ACIDS RES. 17, 6739 (1989) (bovine β lactoglobulin); Vilotte et al., BIOCHIMIE 69, 609-620 (1987) (bovine α-lactalbumin). The structure and function of the various milk protein genes are reviewed by Mercier & Vilotte, J. DAIRY SCI. 76, 3079-3098 (1993) (incorporated by reference in its entirety for all purposes). If additional flanking sequences are useful in optimizing expression, such sequences can be cloned using the existing sequences as probes. Mammary gland-specific regulatory sequences from different organisms can be obtained by screening libraries from such organisms using known cognate nucleotide sequences, or antibodies to cognate proteins as probes.

Useful signal sequences include milk-specific signal sequences or other signal sequences which result in the secretion of eukaryotic or prokaryotic proteins. In some embodiments, the signal sequence is a milk-specific signal sequence, i.e., it is from a gene which encodes a product secreted into milk. In other embodiments, the milk-specific signal sequence is related to the mammary gland-specific promoter used in the construct for mammary gland expression. The size of the signal sequence is not critical. All that is required is that the sequence be of a sufficient size to effect secretion of the desired protein. For example, signal sequences from genes coding for caseins, e.g., alpha, beta, gamma or kappa caseins, beta lactoglobulin, whey acid protein and lactalbumin can be used for mammary gland expression.

A cassette which encodes the transport receptor, therefore, can be assembled as a construct. For example, the construct can include a promoter for a specific tissue, a signal sequence, and DNA encoding the desired protein. A construct can be prepared using methods known in the art. The construct can be prepared as part of a larger plasmid. Such preparation allows the cloning and selection of the correct constructions in an efficient manner. The construct can be located between convenient restriction sites on the plasmid so that they can be easily isolated from the remaining plasmid sequences for incorporation into the desired mammal.

Typically, the constructs used for the insertion of the genes of interest can comprise a marker gene that provides for selection of desired recombinants. Exemplary marker genes include antibiotic resistance markers, drug resistance markers, and green fluorescent protein, among others. The constructs containing two regions of homology to an exogenous immunoglobulin molecule, which flank a positive selection marker (e.g., an antibiotic resistance gene such as neomycin) that is operably linked to a promoter, may be generated using standard molecular biology techniques and used in the methods of the present invention or preparation of the methods provided and related products.

Genetically engineered cell lines can be used to produce a transgenic mammal. As used herein, the term "transgenic cell" refers to a cell containing a transgene. A transgene can be introduced into the cell, directly or indirectly, by introduction into a precursor of the cell, by way of deliberate genetic manipulation, such as by microinjection, infection with a recombinant virus, or via conventional transformation or transfection techniques. As used herein, the terms "transfection" and "transformation" include a variety of techniques for introducing a transgenic sequence into a host cell, including calcium phosphate or calcium chloride co-precipitation, DEAE-dextrane-mediated transfection, lipofection, or electroporation.

A transgenic primary cell line suitable for somatic cell nuclear transfer can be created by transfection of the transgene(s) for the transport receptor and the protein of interest. The two transgene(s) can either contain the same selection marker or alternate markers so that insertion sites and/or expression levels may be determined separately. Markers include neomycin, puromycin, zeocin, hygromycin or any other selectable marker.

Following selection of recombinant colonies, cells can be isolated and expanded, with aliquots frozen for long-term preservation according to procedures known in the field. The selected transgenic cell-lines can be characterized using standard molecular biology methods (e.g., polymerase chain reaction (PCR), Southern blotting, FISH). Cell lines carrying a transgene(s) of the appropriate copy number, generally with a single integration site (although the same technique could be used with multiple integration sites), can then be used as karyoplast donors in a somatic cell nuclear transfer protocol. Following nuclear transfer, and embryo transfer to a recipient animal, and gestation, live transgenic offspring can be obtained. Typically, a transgenic offspring carries only one transgene integration on a specific chromosome, the other homologous chromosome not carrying an integration in the same site. Hence, the transgenic offspring is heterozygous for the transgene. According to one embodiment, a technique that allows for the production of homozygous transgenic animals can be used. Following the birth of the first heterozygous offspring containing a functional transport receptor or protein of interest, a biopsy is performed and a primary cell line is derived from the first offspring. Aliquots of this cell line are then treated and prepared for a second round of transgenesis. Typically, G418, puromycin, hygromycin, zeocin, gancyclovir, FIAU or any other agent able to kill cells in culture and for which a suitable resistance gene is available can be used as a selection marker. Thereafter, nuclear transfer techniques can be utilized to generate additional animals that are homozygous for the desired trait with the animals developed for that gene being homozygous.

According to one embodiment, a transgenic line stably maintaining the transgene for the transport receptor is developed first, and transgenic animals can be developed such that this exogenous gene is stably expressed in sufficient quantities in lactating transgenic mammals. Once this line is developed the cells of this animal can be again used for an insertion of a second transgene encoding, for example, the protein of interest. In some embodiments, a transgenic animal comprising the transgene for the protein of interest is created first, and the transgene encoding the transport receptor is inserted subsequently.

In some embodiments, the production of a non-human transgenic mammal is accomplished with the use of nuclear transfer techniques. In other embodiments, the use of fetal fibroblasts may be preferred over some other somatic cells, as these cells are readily propagated and genetically manipulated in tissue culture. The specific line(s) of any animal used can, in some embodiments, be selected for general good health, good embryo yields, good pronuclear visibility in the embryo, and good reproductive fitness.

In some embodiments, the methods provided include a step of obtaining or collecting milk from a transgenic non-human mammal. In other embodiments, the method also includes a step of separating or purifying a protein of interest from the milk. Also provided, therefore, are purified preparations of the protein of interest as are the proteins of interest in isolated form.

A "purified preparation" or "isolated protein" as used herein, refers to a protein that is substantially free of material with which it occurs in the milk of a transgenic mammal. The protein is, in some embodiments, separated from substances (e.g., gel matrix, such as polyacrylamide) that are used to purify it. In one embodiment, the preparation of a protein has less than about 30% (by dry weight) of non-protein material (material that is not the protein of interest) (also referred to herein as a "milk impurity" or "milk component"), in another embodiment, preferably less than about 20% of non-protein material, in still another embodiment, less than about 10% of non-antibody material, and, in yet another embodiment, less than about 5% non-antibody material. Non-protein material includes casein, lipids (e.g., soluble lipids and phospholipids), lactose and other small molecules (e.g., glucose, galactose), small peptides (e.g., microbial peptides and anti-microbial peptides) and other milk proteins (e.g., whey proteins such as β-lactoglobulin and α-lactalbumin, lactoferrin and serum albumin). The proteins, in one embodiment, constitute at least 10, 20, 50 70, 80 or 95% dry weight of the purified preparation. In another embodiment, the preparation contains at least 1, 10, or 100 μg of the protein or at least 1, 10, or 100 mg of the protein. In addition, in some embodiments, the purified preparation contains about 70%, 75%, 80%, 85%, 90%, 95%, 98% assembled proteins (e.g., assembled antibodies).

Proteins (and fragments thereof) can be isolated from milk using standard protein purification methods known in the art. For example, the methods of Kutzko et al. (U.S. Pat. No. 6,268,487) can be utilized to purify the proteins as provided herein.

As another example, milk proteins are often isolated by a combination of processes. For example, raw milk can first be fractionated to remove fats, for example, by skimming, centrifugation, sedimentation (H. E. Swaisgood, *Developments in Dairy Chemistry*, in: CHEMISTRY OF MILK PROTEIN, Applied Science Publishers, NY, 1982), acid precipitation (U.S. Pat.

No. 4,644,056) or enzymatic coagulation with rennin or chymotrypsin (Swaisgood, ibid.). Next, the major milk proteins may be fractionated into either a clear solution or a bulk precipitate from which the specific protein of interest may be readily purified. As another example, French Patent No. 2,487,642 describes the isolation of milk proteins from skim milk or whey by membrane ultrafiltration in combination with exclusion chromatography or ion exchange chromatography. Whey is first produced by removing the casein by coagulation with rennet or lactic acid. U.S. Pat. No. 4,485,040 describes the isolation of an alpha-lactoglobulin-enriched product in the retentate from whey by two sequential ultrafiltration steps. U.S. Pat. No. 4,644,056 provides a method for purifying immunoglobulin from milk or colostrum by acid precipitation at pH 4.0-5.5, and sequential cross-flow filtration first on a membrane with 0.1-1.2 micrometer pore size to clarify the product pool and then on a membrane with a separation limit of 5-80 kd to concentrate it. U.S. Pat. No. 4,897,465 teaches the concentration and enrichment of a protein such as immunoglobulin from blood serum, egg yolks or whey by sequential ultrafiltration on metallic oxide membranes with a pH shift. Filtration can be carried out first at a pH below the isoelectric point (pI) of the selected protein to remove bulk contaminants from the protein retentate, and next at a pH above the pI of the selected protein to retain impurities and pass the selected protein to the permeate. A different filtration concentration method is taught by European Patent No. EP 467 482 B1 in which defatted skim milk is reduced to pH 3-4, below the pI of the milk proteins, to solubilize both casein and whey proteins. Three successive rounds of ultrafiltration or diafiltration then, in this example, concentrate the proteins to form a retentate containing 15-20% solids of which 90% is protein.

As another example, milk can initially be clarified. A typical clarification protocol can include the following steps:
(a) diluting milk 2:1 with 2.0 M Arginine-HCl pH 5.5;
(b) spinning diluted sample in centrifuge for approximately 20 minutes at 4-8° C.;
(c) cooling samples for approximately 5 minutes on ice to allow fat sitting on top to solidify;
(d) removing fat pad by "popping" it off the top with a pipette tip; and
(e) decanting of supernatant into a clean tube.

Further methods for the purification of proteins are known in the art.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Example 1

A Method for the Production of Transgenic Mammals with Nuclear Transfer

Oocytes

Oocytes can be obtained at various times during an animal's reproductive cycle. Oocytes at various stages of the cell cycle can be obtained and then induced in vitro to enter a particular stage of meiosis. For example, oocytes cultured on serum-starved medium become arrested in metaphase. In addition, arrested oocytes can be induced to enter telophase by serum activation.

Oocytes can be matured in vitro before they are used to form a reconstructed embryo. This process usually requires collecting immature oocytes from mammalian ovaries, e.g., a caprine ovary, and maturing the oocyte in a medium prior to enucleation until the oocyte reaches the desired meiotic stage, e.g., metaphase or telophase. In addition, oocytes that have been matured in vivo can be used to form a reconstructed embryo.

Oocytes can be collected from a female mammal during superovulation. Briefly, oocytes, e.g., caprine oocytes, can be recovered surgically by flushing the oocytes from the oviduct of the female donor. Methods of inducing superovulation in goats, and the collection of caprine oocytes is described herein.

Cytoplast Preparation and Enucleation

Oocytes can be treated with cytochalasin-B (Sigma, 5 μg/ml in synthetic oviductal fluid (SOF) with 10% fetal bovine serum (FBS)) 15 to 30 minutes prior to enucleation. Metaphase-II stage oocytes can be enucleated with a 25 to 30 μm glass pipette by aspirating the first polar body and adjacent cytoplasm surrounding the polar body (~30% of the cytoplasm) to remove the metaphase plate. After enucleation, oocytes can be immediately reconstructed.

Nuclear Transfer and Reconstruction

Donor cell injection is conducted in the same medium used for oocyte enucleation. One donor cell is placed between the zona pellucida and the ooplasmic membrane using a glass pipet. The cell-oocyte couplets is incubated in SOF for 30 to 60 minutes before electrofusion and activation procedures. Reconstructed oocytes are equilibrated in fusion buffer (300 mM mannitol, 0.05 mM $CaCl_2$, 0.1 mM $MgSO_4$, 1 mM $K_2HPO_4$, 0.1 mM glutathione, 0.1 mg/ml bovine serum albumin (BSA)) for 2 minutes. Electrofusion and activation are conducted at room temperature, in a fusion chamber with 2 stainless steel electrodes fashioned into a "fusion slide" (500 μm gap; BTX-Genetronics, San Diego, Calif.) filled with fusion medium.

Fusion is performed using a fusion slide. The fusion slide is placed inside a fusion dish, and the dish is flooded with a sufficient amount of fusion buffer to cover the electrodes of the fusion slide. Couplets are removed from the culture incubator and washed through fusion buffer. Using a stereomicroscope, couplets are placed equidistant between the electrodes, with the karyoplast/cytoplast junction parallel to the electrodes. It should be noted that the voltage range applied to the couplets to promote activation and fusion can be from 1.0 kV/cm to 10.0 kV/cm. Preferably however, the initial single simultaneous fusion and activation electrical pulse has a voltage range of 2.0 to 3.0 kV/cm, most preferably at 2.5 kV/cm, preferably for at least 20 μsec duration. This is applied to the cell couplet prior to fusion and/or activation using a BTX ECM 2001 Electrocell Manipulator. The duration of the micropulse can vary from 10 to 80 μsec. After the process the treated couplet is typically transferred to a drop of fresh fusion buffer. Fusion treated couplets are washed through equilibrated SOF/FBS, then transferred to equilibrated SOF/FBS with or without cytocholasin-B. If cytocholasin-B is used, its concentration can vary from 1 to 15 μg/ml, most preferably at 5 μg/ml. The couplets are incubated at 37-39° C. in a humidified gas chamber containing approximately 5% $CO_2$ in air. It should be noted that mannitol may be used in the place of cytocholasin-B (HEPES-buffered mannitol (0.3 mm) based medium with $Ca^{+2}$ and BSA).

Nuclear Transfer Embryo Culture and Transfer to Recipients

Nuclear transfer embryos are cultured in 50 μl droplets of SOF with 10% FBS overlaid with mineral oil. Embryo cultures are maintained in a humidified 39° C. incubator with 5% $CO_2$ for 48 hours before transfer of the embryos to recipient does. Recipient embryo transfer are performed as described (Baguisi et al., 1999).

Transfer of Reconstructed Embryos

A reconstructed embryo can be transferred to a recipient and allowed to develop into a cloned or transgenic mammal. For example, the reconstructed embryo can be transferred via the fimbria into the oviductal lumen of each recipient. In addition, methods of transferring an embryo to a recipient mammal are known in the art and described, for example, in Ebert et al. (1994) *Bio/Technology* 12:699.

Example 2

A Method for the Production of Transgenic Mammals with Microinjection

Goat Species and Breeds

Swiss origin goats, e.g., the Alpine, Saanen, and Toggenburg breeds, are useful in the production of transgenic goats. Below exemplary steps for the production of transgenic goats are briefly described. These steps include superovulation of female goats, mating to fertile males and collection of fertilized embryos. Once collected, pronuclei of one-cell fertilized embryos are microinjected with DNA constructs. All embryos from one donor female are, in some embodiments, kept together and transferred to a single recipient female, if possible.

Goat Superovulation

The timing of estrus in the donors is synchronized on Day 0 by 6 mg subcutaneous norgestomet ear implants (Syncromate-B, CEVA Laboratories, Inc., Overland Park, Kans.). Prostaglandin is administered after the first seven to nine days to shut down the endogenous synthesis of progesterone. Starting on Day 13 after insertion of the implant, a total of 18 mg of follicle-stimulating hormone (FSH—Schering Corp., Kenilworth, N.J.) is given intramuscularly over three days in twice-daily injections. The implant is removed on Day 14. Twenty-four hours following implant removal the donor animals are mated several times to fertile males over a two-day period (Selgrath, et al., Theriogenology, 1990. pp. 1195-1205).

Embryo Collection

Surgery for embryo collection occurs on the second day following breeding (or 72 hours following implant removal). Superovulated does are removed from food and water 36 hours prior to surgery. Does are administered 0.8 mg/kg Diazepam (Valium®), IV, followed immediately by 5.0 mg/kg Ketamine (Keteset), IV. Halothane (2.5%) is administered during surgery in 2 L/min oxygen via an endotracheal tube. The reproductive tract is exteriorized through a midline laparotomy incision. Corpora lutea, unruptured follicles greater than 6 mm in diameter, and ovarian cysts are counted to evaluate superovulation results and to predict the number of embryos that should be collected by oviductal flushing. A cannula is placed in the ostium of the oviduct and held in place with a single temporary ligature of 3.0 Prolene. A 20 gauge needle is placed in the uterus approximately 0.5 cm from the uterotubal junction. Ten to twenty ml of sterile phosphate buffered saline (PBS) are flushed through the cannulated oviduct and collected in a Petri dish. This procedure is repeated on the opposite side and then the reproductive tract is replaced in the abdomen. Before closure, 10-20 ml of a sterile saline glycerol solution is poured into the abdominal cavity to prevent adhesions. The linea alba is closed with simple interrupted sutures of 2.0 Polydioxanone or Supramid and the skin closed with sterile wound clips.

Fertilized goat eggs are collected from the PBS oviductal flushings on a stereomicroscope and are then washed in Ham's F 12 medium (Sigma, St. Louis, Mo.) containing 10% fetal bovine serum (FBS) purchased from Sigma. In cases where the pronuclei are visible, the embryos is immediately microinjected. If pronuclei are not visible, the embryos are placed in Ham's F12 containing 10% FBS for short term culture at 37° C. in a humidified gas chamber containing 5% $CO_2$ in air until the pronuclei become visible (Selgrath, et al., Theriogenology, 1990. pp. 1195-1205).

Microinjection Procedure

One-cell goat embryos are placed in a microdrop of medium under oil on a glass depression slide. Fertilized eggs having two visible pronuclei are immobilized on a flame-polished holding micropipet on a Zeiss upright microscope with a fixed stage using Normarski optics. A pronucleus is microinjected with the DNA construct of interest, e.g., a BC355 vector containing a coding sequence of interest operably linked to the regulatory elements of the goat beta-casein gene, in injection buffer (Tris-EDTA) using a fine glass microneedle (Selgrath, et al., Theriogenology, 1990. pp. 1195-1205).

Embryo Development

After microinjection, the surviving embryos are placed in a culture of Ham's F12 containing 10% FBS and then incubated in a humidified gas chamber containing 5% $CO_2$ in air at 37° C. until the recipient animals are prepared for embryo transfer (Selgrath, et al., THERIOGENOLOGY, 1990. p. 1195-1205).

Preparation of Recipients

Estrus synchronization in recipient animals is induced by 6 mg norgestomet ear implants (Syncromate-B). On Day 13 after insertion of the implant, the animals are given a single non-superovulatory injection (400 I.U.) of pregnant mares serum gonadotropin (PMSG) obtained from Sigma. Recipient females are mated to vasectomized males to ensure estrus synchrony (Selgrath, et al., THERIOGENOLOGY, 1990. pp. 1195-1205).

Embryo Transfer

All embryos from one donor female are kept together and transferred to a single recipient when possible. The surgical procedure is identical to that outlined for embryo collection outlined above, except that the oviduct is not cannulated, and the embryos are transferred in a minimal volume of Ham's F12 containing 10% FBS into the oviductal lumen via the fimbria using a glass micropipet. Animals having more than six to eight ovulation points on the ovary are deemed unsuitable as recipients. Incision closure and post-operative care are the same as for donor animals (see, e.g., Selgrath, et al., Theriogenology, 1990. pp. 1195-1205).

Monitoring of Pregnancy and Parturition

Pregnancy is determined by ultrasonography 45 days after the first day of standing estrus. At Day 110 a second ultrasound exam is conducted to confirm pregnancy and assess fetal stress. At Day 130 the pregnant recipient doe is vaccinated with tetanus toxoid and Clostridium C&D. Selenium and vitamin E (Bo-Se) are given IM and Ivermectin was given SC. The does are moved to a clean stall on Day 145 and allowed to acclimatize to this environment prior to inducing labor on about Day 147. Parturition is induced at Day 147 with 40 mg of PGF2a (Lutalyse®, Upjohn Company, Kalamazoo Mich.). This injection is given IM in two doses, one 20 mg dose followed by a 20 mg dose four hours later. The doe is under periodic observation during the day and evening following the first injection of Lutalyse® on Day 147. Observations are increased to every 30 minutes beginning on the morning of the second day. Parturition occurred between 30 and 40 hours after the first injection. Following delivery the doe is milked to collect the colostrum and passage of the placenta is confirmed.

Verification of the Transgenic Nature of $F_0$ Animals

To screen for transgenic $F_0$ animals, genomic DNA is isolated from two different cell lines to avoid missing any mosaic transgenics. A mosaic animal is defined as any goat that does not have at least one copy of the transgene in every cell. Therefore, an ear tissue sample (mesoderm) and blood sample are taken from a two day old $F_0$ animal for the isolation of genomic DNA (Lacy, et al., A LABORATORY MANUAL, 1986, Cold Springs Harbor, N.Y.; and Herrmann and Frischauf, METHODS ENZYMOLOGY, 1987. 152: pp. 180-183). The DNA samples are analyzed by the polymerase chain reaction (Gould, et al., Proc. Natl. Acad. Sci, 1989. 86:pp. 1934-1938) using primers and by Southern blot analysis (Thomas, Proc. Natl. Acad. Sci., 1980. 77:5201-5205) using a random primed cDNA probe (Feinberg and Vogelstein, Anal. Bioc., 1983. 132: pp. 6-13). Assay sensitivity is estimated to be the detection of one copy of the transgene in 10% of the somatic cells.

For example, Southern blot analysis of the founder male and the three transgenic offspring can be used to see if there is no rearrangement or change in the copy number between generations. The blots can be analyzed on a Betascope 603 and copy number for expression in the mammary gland determined by comparison of the transgene to the goat beta casein endogenous gene.

Evaluation of Expression Levels

The expression level of the transgenic protein, in the milk of transgenic animals, can be determined using enzymatic assays or Western blots.

Generation and Selection of Production Herd

The procedures described above can be used for production of transgenic founder ($F_0$) goats, as well as other transgenic goats. The transgenic $F_0$ founder goats, for example, are bred to produce milk, if female, or to produce a transgenic female offspring if it is a male founder. This transgenic founder male, can be bred to non-transgenic females, to produce transgenic female offspring.

Example 3

G418 Selection for Recombinant Human FcRn Gene Insertion

Plate primary cells at $2 \times 10^5/10$ cm petri dish. Set up 2 petris for every concentration of G418. Optimum concentrations of G418 will vary from cell line to cell line, for example:
1.2"
1.5"
2.0"
2.5"
3.0"

Add the drug at the same time you plate the cells. There is no need to let the cells settle down first. Feed plates daily for the next five days with fresh medium+drug. After ~5 days most of the cells will be dead, so feeding can be dropped back to every other day or so. Pick 6-24 of the best looking clones from the highest concentration of G418 onto 24-well wells. Freeze and expand for DNA and karyotyping. Immobilize cells on filters for interphase FISH.

Example 4

Expression of CTLA4IgG4

CTLA4IgG4 Constructs

CTLA4IgG4 is CTLA4 with 2 N-linked 4 glycosylation sites (Schwartz, J. Nature 401:604-8, 2001) fused to the Fc portion of an IgG4 molecule, which also has a glycosylation on each Fc domain. This fusion protein had been expressed previously in the mammary gland and was shown to have only partial sialation. To produce CTLA4IgG4 in the blood stream, the fusion protein is expressed by placing it under the control of the human serum albumin (HSA) promoter obtained described by Pinkert et al., Genes Dev. 1987, 1: 286-76.

Figure 3:
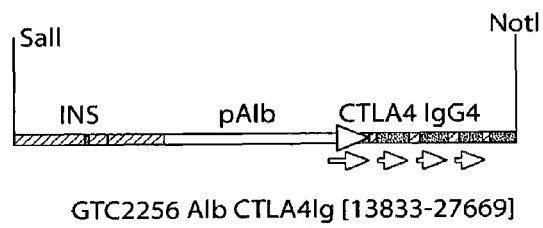
FIG. 3 shows a construct for the expression of CTLA4IgG4.
Figure 4:
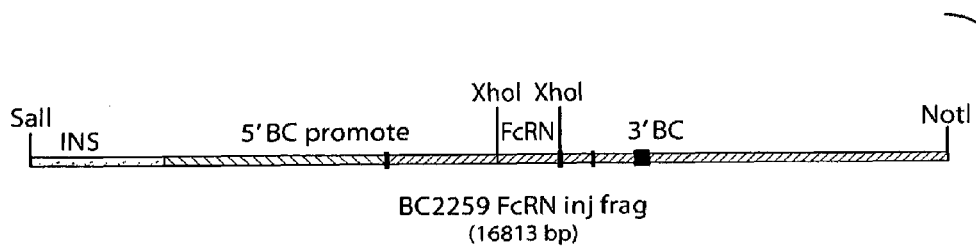
FIG. 4 shows constructs for the expression of FcRn and beta-2 microglobulin (β2M).
Figure 4:
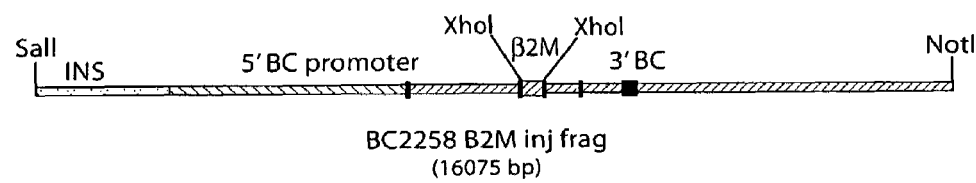

The HSA promoter was obtained as a 2.3 kb fragment containing the genomic sequence upstream of the transcriptional start site of the HSA protein. This fragment was linked to an insulator sequence, to insure proper expression, followed by the sequence of the bgh poly A signal (Chung et al. 1993. Cell 74, 505-514). Into this albumin promoter vector a fragment encoding CTLA4IgG4 was inserted (Schwartz, et al. 2001, Nature, 410:604). The expression constructs are shown in FIGS. 3 and 4.

The FcRn constructs were generated such that the receptor is expressed under control of the beta casein promoter to allow for expression of the FcRn during lactation. The FcRn is made up of two proteins, (FcRn and β-2 microglobulin). The cDNA for FcRn was obtained from a commercial source (Origene, Rockville, Md.), and the β-2 microglobulin was synthesized by Blue Heron (Bothell, Wash.) from the published sequence (GenBank Accession No. NM_004048). The constructs were ligated into a beta casein vector. These constructs were subsequently used to developed non-human mammals expressing functional FcRn in the mammary gland.

Generation of Transgenic Mice

The vectors described above were micro-injected into mouse embryos. Representative animals containing the CTLA4IgG4 alone and those carrying the FcRn constructs alone were identified.

TABLE 1

| Mice expressing CTLA4IgG4 | | | |
|---|---|---|---|
| | CTLA4 Ig in mouse milk | | |
| mouse | FcRn | B2m | CTLA4 Ig |
| 125 | + | + | + |
| 126 | -- | -- | + |

Mouse #125 and #126 were tested for the ability of the albumin promoter to secrete CTLA4IgG4. There was significant expression of the protein in the blood of #125 and #126 transgenic animals, and both have the same level of expression. The level that was secreted into the milk of the lactating females was then determined. As shown in the Western blot (FIG. 5), there is more CTLA4IgG4 in the mouse without the FcRn, compared to the animal trangenic for FcRn. Just as has been shown in the mouse, FcRn appears to pump proteins out of the milk via FcRn, which is opposite of the transport direction expected of ruminants. This is evidenced by the lower level in the milk of the FcRn and β2M containing mice #125 than in the control #126. The results demonstrate the successful expression of FcRn and CTLA4IgG4 as well as the transport of CTLA4IgG4 via FcRn. Therefore, the results show that FcRn does function in the mammary gland by binding and transporting CTLA4IgG4.

The results here show that in mice the FcRn transports proteins comprising an Fc domain consistent with Cianga P, et al. Identification and function of neonatal Fc receptor in mammary gland of lactating mice. Eur J Immunol 1999; 29:2515-23.

It is to be understood that, while the invention has been described in conjunction with the detailed description thereof, the foregoing description is intended to illustrate and not limit the scope of the invention. Other aspects, advantages, and modifications are within the scope of the following claims.

References

The listing of the references in the following list is not intended to be an admission that any of the references is a prior art reference.

Alzari, P. M. et al., *Three-Dimensional Structure of Antibodies*. ANN. REV. IMMUNOL. 1988 6:555-80.

Baguisi A, (1999) et al., *Production of Goats by Somatic Cell Nuclear Transfer*, NATURE BIOTECH; 17: 456-461.

Chung et al. 1993. *Cell*, 74, 505-514

Colcher D, et al., *Effects of Genetic Engineering on the Pharmacokinetics of Antibodies*. QJ NUCL MED 1999; 43:132-9.

Crowe J. S., et al., *Humanized Monoclonal Antibody CAMPATH-1H: Myeloma Cell Expression of Genomic Constructs, Nucleotide Sequence of cDNA Constructs and Comparison of Effector Mechanisms of Myeloma and Chinese Hamster Ovary Cell Derived Material*. CLIN EXP IMMUNOL (1992);87: 105-10.

Davis, G. T. et al., *Single Chain Antibody (SCA) Encoding Genes: One-Step Construction and Expression in Eukaryotic Cells*. BIO/TECHNOL. 1991 9:165-69.

Ghetie V., et al., *FcRn: the MHC Class I-related Receptor that is More than an IgG Transporter*, IMMUNOL TODAY. (1997); 18:592-98.

Harlow, E., and D. Lane, ANTIBODIES: A LABORATORY MANUAL. (Cold Spring Harbor, N.Y.: Cold Spring Harbor Laboratory. (1988)).

Jakobovits, A. L. et al., *Expression of Human Immunoglobulin Loci-Derived YACs in Mice: Towards Mice Producing A Large Repertoire Of Human Antibodies*. J. CELL. BIOCHEM. ABSTR. SUPPL. 18D 1994 (Abstract T-017):185.

Junghans R. P. and Anderson C. L., *The Protection Receptor for IgG Catabolism is the B2-Microglobulin-Containing Neonatal Intestinal Transport Receptor*, PROC NATL ACAD SCI USA. (1996);96:5512-16.

Junghans R. P., *Finally! The Brambell Receptor (FcRB): Mediator of Transmission of Immunity and Protection from Catabolism for IgG*, IMMUNOL RES. (1997);16:29-57.

Kim K. J. et al., *Net Absorption of IgG via FcRn-Mediated Transcytosis Across Rat Alveolar Epithelial Cell Monolayers*, AM J PHYSIOL LUNG CELL MOL PHYSIOL. (September 2004) 287 (3):L616-22. (Abstract)

Kuroiwa Y., et al., *Manipulation of Human Minichromosomes to Carry Greater than Megabase-Sized Chromosome Inserts*. NAT BIOTECHNOL. (2000);18:1086-90.

Lantto J. et al., *Chain Shuffling to Modify Properties of Recombinant Immunoglobulins*.

Leach J. L. et al., *Isolation from Human Placenta of the IgG Transporter, FcRn, and Localization to the Syncytiotrophoblast: Implications for Maternal-Fetal Antibody Transport*, J. IMMUNOLOGY, (1996)(vol 157)(8):3317-22, Maniatis, T. et al., MOLECULAR CLONING: A LABORATORY MANUAL. (2nd ed. Cold Spring Harbor, N.Y.: Cold Spring Harbor Laboratory (1989)).

Ober, R. J. et al., *Exocytosis of IgG as Mediated by the Receptor, FcRn: an Analysis at the Single-Molecule Level*, PROC. NATL. ACAD. SCI. USA, (2004) 101:11076-81.

Padlan, E. A., *Anatomy of the Antibody Molecule*, MOL. IMMUNOL. 31(3):169-217 (1994).

Pinkert et al., *Genes Dev.* 1987, 1: 286-76.

Reff M. E., et al., *Depletion of B cells In Vivo by a Chimeric Mouse Human Monoclonal Antibody to CD20*. BLOOD (1994); 83:435-45.

Wagner S. D., et al., *Antibodies Generated from Human Immunoglobulin Miniloci in Transgenic Mice*. NUCLEIC ACIDS RES., (1994);22:1389-93.

Whitlow M. B. et al., *An Improved Linker For Single-Chain Fv With Reduced Aggregation and Enhanced Proteolytic Stability*. PROTEIN ENG. (1993) 6(8):989-95.

Worn A., et al., *Stability Engineering of Antibody Single-Chain Fv fragments*. J MOL BIOL 2001; 305:989-1010.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims and Summary of the Invention section provided herein.

We claim:

1. A non-human transgenic mammal whose genome comprises a DNA sequence encoding human FcRn and a DNA sequence encoding beta-microglobulin operably linked to a mammary gland-specific promoter, and further comprises a DNA sequence encoding a transgenic protein comprising a human Fc-domain operably linked to a non-mammary gland-specific promoter.

2. The non-human mammal of claim 1, wherein the non-mammary gland-specific promoter is a liver-specific promoter.

3. The non-human mammal of claim 2, wherein the liver-specific promoter is an albumin promoter.

4. The non-human mammal of claim 1, wherein the transgenic protein is an antibody.

5. A composition comprising milk obtained from the non-human mammal of claim 1.

6. A method for obtaining a transgenic protein comprising a human Fc-domain, comprising:
    generating a non-human transgenic mammal whose genome comprises a DNA sequence encoding human FcRn and a DNA sequence encoding beta-microglobulin operably linked to a mammary gland-specific promoter, and further comprises a DNA sequence encoding transgenic protein comprising a human Fc-domain operably linked to a non-mammary gland-specific promoter, wherein the transgenic protein comprising a human Fc-domain binds the functional human FcRn via the human Fc-domain,
    collecting milk from the non-human mammal, and
    separating the transgenic protein comprising a human Fc-domain from the milk.

7. The method of claim 6, wherein the non-mammary gland-specific promoter is a liver-specific promoter.

8. The method of claim 7, wherein the liver-specific promoter is an albumin promoter.

9. The method of claim 6, wherein the transgenic protein comprising a human Fc-domain is an antibody.

10. A composition comprising the collected milk of the method of claim 6.

11. A composition comprising milk from a non-human transgenic mammal whose genome comprises a DNA sequence encoding human FcRn and a DNA sequence encoding beta-microglobulin operably linked to a mammary gland-specific promoter, and further comprises a DNA sequence encoding a transgenic protein comprising a human Fc-domain operably linked to a non-mammary gland-specific promoter.

12. The composition of claim 11, wherein the glycosylation pattern of the transgenic protein is different from the glycosylation pattern of the protein when expressed in the mammary gland of the non-human mammal.

* * * * *